(12) United States Patent
Li et al.

(10) Patent No.: US 7,626,044 B2
(45) Date of Patent: Dec. 1, 2009

(54) TRIPTOLIDE DERIVATIVES AND THEIR USES

(75) Inventors: Yuanchao Li, Shanghai (CN); Jianping Zuo, Shanghai (CN); Fan Zhang, Shanghai (CN); Ru Zhou, Shanghai (CN); Jian Ding, Shanghai (CN)

(73) Assignees: Shanghai Institute of Materia Medica Chinese Academy of Sciences, Shanghai (CN); Shanghai Pharmaceutical (Group) Co., Ltd., Shanghai (CN)

( * ) Notice: Subject to any disclaimer, the term of this patent is extended or adjusted under 35 U.S.C. 154(b) by 457 days.

(21) Appl. No.: 10/540,908

(22) PCT Filed: Jan. 28, 2003

(86) PCT No.: PCT/CN03/00095

§ 371 (c)(1),
(2), (4) Date: Jan. 29, 2007

(87) PCT Pub. No.: WO2004/058770

PCT Pub. Date: Jul. 15, 2004

(65) Prior Publication Data

US 2007/0197476 A1  Aug. 23, 2007

(30) Foreign Application Priority Data

Dec. 27, 2002  (CN) ............... 02 1 60524

(51) Int. Cl.
*C07D 307/77* (2006.01)
*C07F 9/06* (2006.01)
(52) U.S. Cl. ..................... 549/297; 549/218
(58) Field of Classification Search ........... 549/297, 549/218
See application file for complete search history.

(56) References Cited

FOREIGN PATENT DOCUMENTS

| CN | 1257507 A | 6/2000 |
|----|-----------|--------|
| CN | 1095844 C | 12/2002 |
| CN | 1133637 C | 1/2004 |

OTHER PUBLICATIONS

Progress in research on triptolide (in Chinese), China Journal of Chinese Materia Medica, vol. 30, Issue 3, 170-174, Feb. 2005.
Progress in structure modification of triptolide (in Chinese), Acta Pharmaeutica Sinica 2004, 39(10), 857-864.
Advances in pharmacological research of *Tripterygium Wilfordii* Hook. f. on immune system and inflammatory reaction (in Chinese), Chinese Journal of New Drugs 2004, vol. 13 No. 9, 780-784.
Enantioselective Total Synthesis of (−)-Triptolide, (−)-Triptonide, (+)-Triptophenolide, and (+)-Triptoquinonide, J. Org. Chem., vol. 65, No. 7. 2000, 2208-2217.
Triptolide suppresses proinflammatory cytokine-induced matrix metalloproteinase and aggrecanase-1 gene expression in chondrocytes, A. Liacini et l Biochemical and Biophysical Research Communications 327 (2005) 320-327.
Triptolide inhibits transcription factor NF-kappaB and induces apoptosis of multiple myeloma cells, Leukemia Research 29 (2005) 99-105.
Triptolide, an Active Component of the Chinese Herbal Remeedy *Tripterygium wilfordii* Hook F, Inhibits Production of Nitric Oxide by Decreasing Inducible Intric Oxide Synthase Gene Transcript, Arthritis & Rheumatism, vol. 50, No. 9, 2004, 2995-3003.

*Primary Examiner*—D. Margaret Seaman
*Assistant Examiner*—Nizal S Chandrakumar
(74) *Attorney, Agent, or Firm*—Butzel Long

(57) ABSTRACT

Triptolide derivatives of Formula (I), their pharmaceutically acceptable salts and optical isomers, Formula (I):

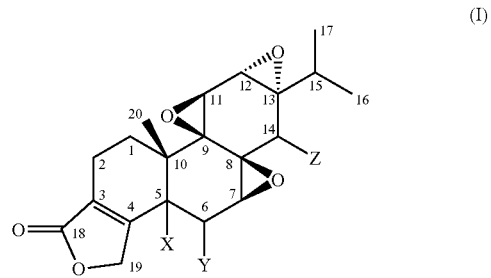

wherein, C5 and C6 are connect with each other by a C-C single bond or double bond; when C5 and C6 are connected with C-C single bond, X and Y represent independently hydrogen, oxygen, hydroxyl, halogen, lower alkyl-oxy, lower alkyl-amino, mercapto, lower alkyl-thio, the group of formula —OCOR, —OSO$_2$OR or —OPO(OH)$_2$, each of which is attached to C5 and C6, R represents —(CH$_2$)nCO$_2$Na, —(CO$_2$)nCO$_2$K, or —(CH$_2$)nCH$_3$, wherein n=1-6; Z represents hydrogen, oxygen, hydroxyl, halogen, lower alkyl-oxy, lower alkyl-amino, mercapto, lower alkyl-thio, the group of formula -OCOR, -OSO$_2$OR or —OPO(OH)2, each of which is linked at C14-position, R represents —(CH2)nCO2Na, —(CO2)nCO2K, or —(CH$_2$)nCH$_2$, wherein n=1-6; wherein, the"_____" linked with X, Y, and Z represents the stereochemistry orientations "⬛" or "⬚" , but X and Y cannot both be hydrogen atom at the same time, methods for preparing the triptolides and their use as antiphiogistic agent, immunosuppressive agent or therapeutic agent for other related diseases.

7 Claims, 11 Drawing Sheets

A. Vehicle treatment

B. LLDT-8 1 mg/kg treatment

TRIPTOLIDE DERIVATIVES AND THEIR USES

RELATED APPLICATIONS

The present application is a 35 U.S.C. §371 national stage filing of International Patent Application No. PCT/CN2003/000095, filed Jan. 28, 2003, through which and to which priority is claimed to Chinese Priority Patent Application No. 02160524.6, filed Dec. 27, 2002.

FIELD OF THE INVENTION

The present invention relates to chemical structure modification and biological activity studies of active components in natural medicine, which mainly involved the process for preparing novel derivatives of triptolide, a diterpenoid lactone isolated from *Tripterygium Wilfordii* Hook f and studies on their immunosuppressive and anti-flammable activities.

BACKGROUND OF THE INVENTION

*Tripterygium Wilfordii* Hook f(Lei Gong Teng) is a kind of vine plant of the Celastraceae family, and mainly grows under humid conditions near the forest in the Yangtze River basin and southeast area of China. Its major chemical components include diterepenes, triterpenes, sesquiterpenes, alkaloids and so on. Pharmacological studies conducted in the last twenty years demonstrated that the extract of *Tripterygium Wilfordii* Hook f has anti-flammable, immunosuppressive, male sterile, anti-tumor and antibacterial activities. One diterpenoid lactone in *Tripterygium Wilfordii* Hook f, triptolide (shown below), was found to have significant biological activity, especially in respect to its inhibiting immune function.

However, the high toxicity of triptolide limited its clinic uses, and after studying the structure-activity relationship of triptolide thoroughly, the present inventors designed and synthesized a series of novel triptolide derivatives through chemical modification on structure moiety of this lead compound to complete the present invention.

Therefore, the present invention provides highly bioactive triptolide derivatives with low toxicity.

The present invention also provides the application of triptolide derivatives in preparing anti-flammable agents, immunosuppressant agents and other pharmaceutical compositions used in treating related diseases.

SUMMARY OF THE INVENTION

The triptolide derivatives provided by the present invention are compounds having the structure represented by the formula (1) shown as below, or pharmaceutically acceptable salts thereof, or their optical diastereoisomers:

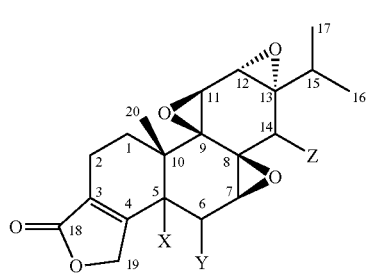

(1)

Wherein C-5 and C-6 are connected through single or double carbon-carbon bond;

When C-5 and C-6 are connected by single bond, X and Y independently represent hydrogen, oxygen, hydroxyl, halogen, alkoxy, mercapto, —$NR_1R_2$, —SR, —OCOR, —$OSO_2OR$, or —$OPO(OH)_2$ linked to C-5 or C-6, wherein R represents —$(CH_2)_nCO_2Na$, —$(CH_2)_nCO_2K$ or —$(CH_2)_nCH_3$, and n=1-6;

Z represents hydrogen, oxygen, hydroxyl, halogen, alkoxy, mercapto, —$NR_1R_2$, —SR, —OCOR, —$OSO_2OR$, or —$OPO(OH)_2$ linked to C-14, wherein R represents —$(CH_2)nCO_2Na$, —$(CH2)nCO_2K$ or —$(CH_2)_nCH_3$, n=1-6;

In the above formula (1), "—" that attaches to "X", "Y" and "Z" represents the stereochemistry orientations "◂▬▸" and "▬▬▸" well;

X and Y are not allowed to be hydrogen at the same time.

The present invention also provides the application of triptolide derivatives as represented by the formula (1), in preparing antiflamable agents, immunosuppressant agents and other pharmaceutical compositions used in treating related diseases.

DETAILED DESCRIPTION OF THE INVENTION

The first type of compounds of the present invention are triptolide derivatives represented by formula (1), where the configuration of X is α (R), that of Y is R or S, and Z is β-OH(R) shown as formula (2):

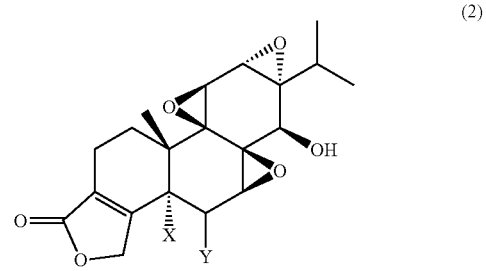

(2)

Wherein the definition of X and Y is identical with the above description.

The second type of compounds of the present invention are triptolide derivatives represented by formula (1), where the configuration of X is α (R) that of Y is R or S, and Z is α-OH(S) shown as formula (3):

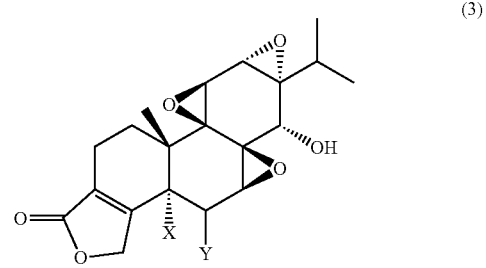

(3)

Wherein the definition of X and Y is identical with the above description.

The third type of compounds of the present invention are triptolide derivatives represented by formula (1), where the configuration of X is a (R) that of Y is R or S, and Z is O shown as formula (4):

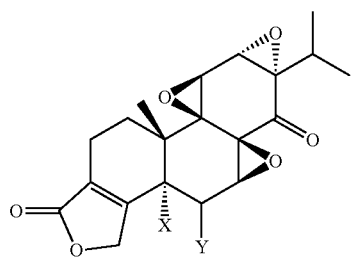

(4)

Wherein the definition of X and Y is identical with the above description.

The fourth type of compounds of the present invention are triptolide derivatives represented by formula (1), where C-5 and C-6 are connected by double bond, and the configuration of Z is R or S, or Z is O shown as formula (5):

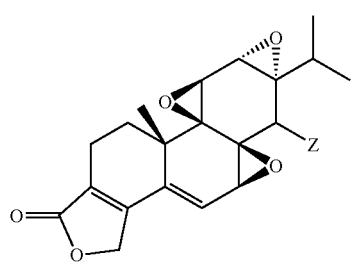

(5)

Wherein the definition of Z is identical with the above description.

The synthetic route used to produce the triptolide derivatives according to the present invention is shown below:

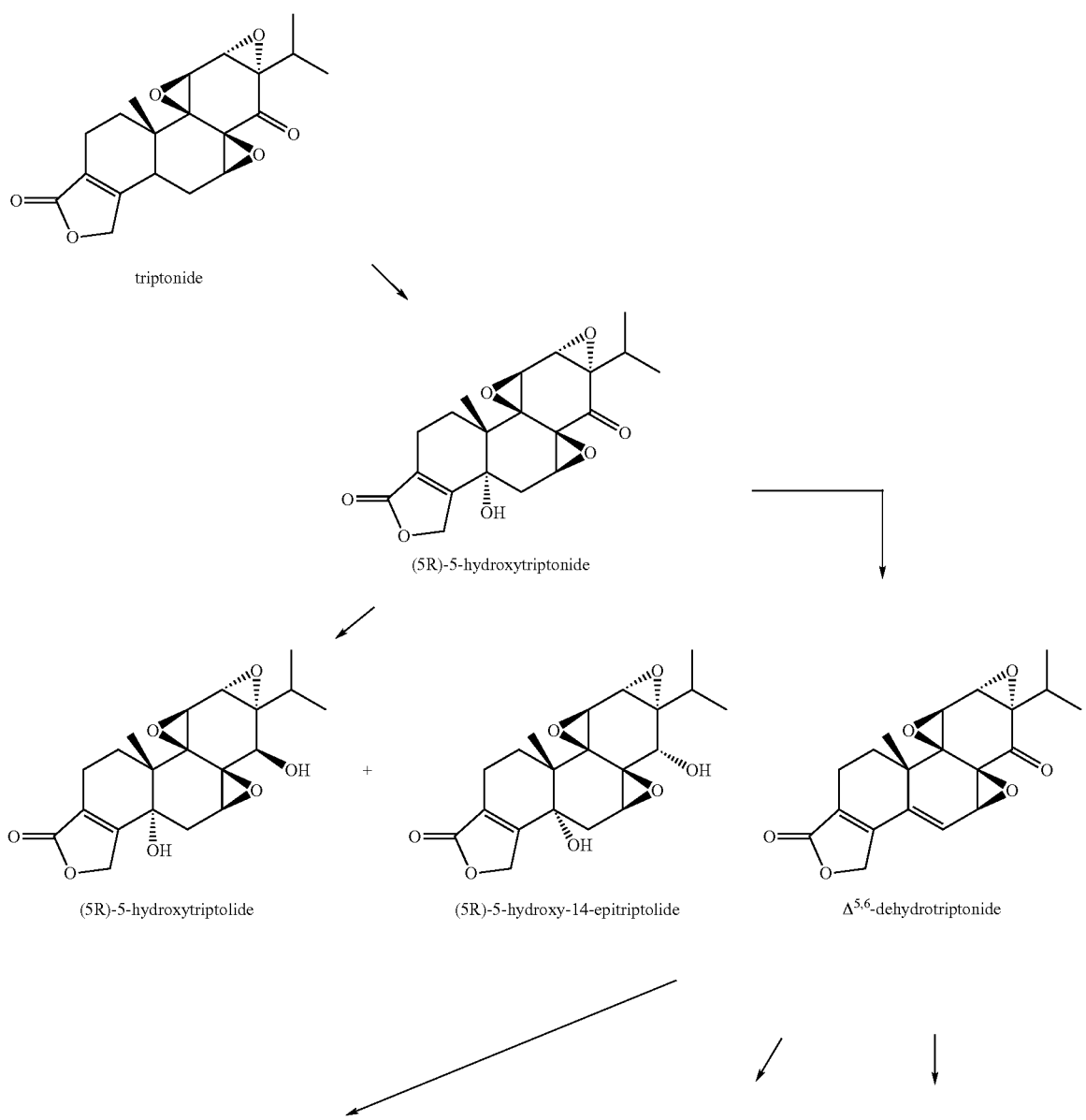

-continued

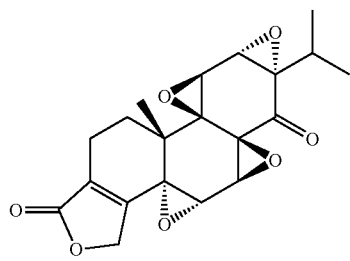

'(5R,6S)-5,6-epoxytriptonide

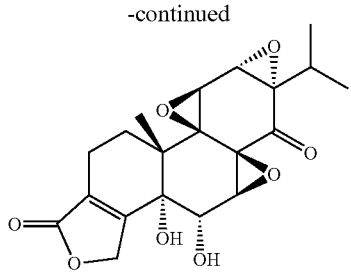

cis-(5R£-6S)-dihydroxytriptonide

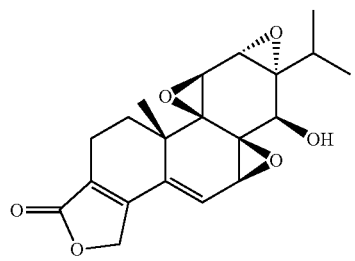

$\Delta^{5,6}$-dehydrotriptolide

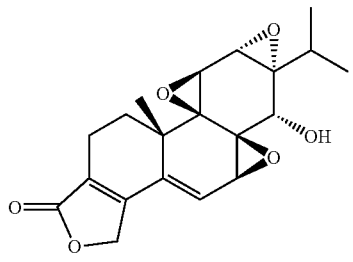

$\Delta^{5,6}$-dehydro-14-epitriptolide

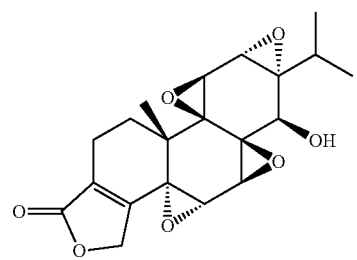

(5R,6S)-5,6-epoxytriptolide

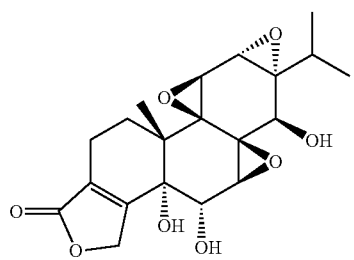

cis-(5R£-6S)-5,6-dihydroxytriptolide

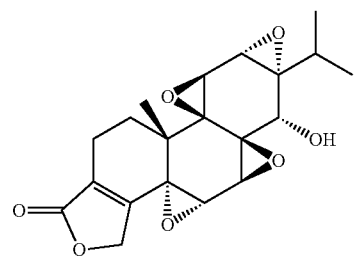

(5R,6S)-5,6-epoxy-14-epitriptolide

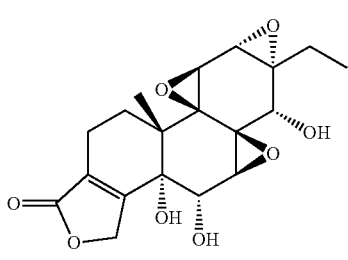

cis-(5R£-6S)-5,6-dihydroxy-14-epitriptolide

In this synthetic route, triptonide, which was used as the starting material was heated with selenium dioxide hydroxylation in nonprotonic polar solvent to give (5R)-5-hydroxytriptonide (LLDT-13), and then reduced in polar protonic solvent to afford (5R)-5-hydroxytriptolide (LLDT-8) and (5R)-5-hydroxy-14-epitriptolide (LLDT-14). Dehydration of (5R)-5-hydroxytriptonide with trifluoroacetic acid anhydride in nonprotic polar solvent gave $\Delta^{5,6}$-dehydrotriptonide (LLDT-15), which was then reduced in polar proton solvent to produce $\Delta^{5,6}$-dehydrotriptolide (LLDT-18) and $\Delta^{5,6}$-dehydro-14-epitriptolide (LLDT-19). $\Delta^{5,6}$-Dehydrotriptonide was reacted with peroxide in polar solvent to give (5R, 6S)-5,6-epoxytriptonide (LLDT-16) by introducing epoxy function group between C-5 and C-6, and was then reduced in polar protonic solvent to provide (5R, 6S)-5,6-epoxytriptolide (LLDT-20) and (5R, 6S)-5,6-epoxy-14-epitriptolide (LLDT-21). Dihydoxylation of $\Delta^{5,6}$-dehydrotriptonide catalysed by osmium tetroxide or osmic acid in polar solvent provided cis-(5R, 6S)-5,6-dihydroxytriptonide (LLDT-17), which was then reduced in protonic polar solvent to give cis-(5R, 6S)-5,6-dihydroxytriptolide (LLDT-22) and cis-(5R, 6S)-5,6-dihydroxy-14-epitriptolide (LLDT-23).

The terms used in the invention have the following meanings:

"Lower alkyl" refers to branched or linear alkyl groups having one to six carbon atoms;

"Alkoxy" refers to methoxy, ethoxy, propoxy, isopropoxy, n-butoxy, iso-butoxy, sec-butoxy, tert-butoxy, n-pentoxy, iso-pentoxy, tert-pentoxy, neo-pentoxy, 2-methyl-butoxy, 1,2-dimethyipropoxy, 1-ethyipropoxy, hexoxy, where methoxy and ethoxy are preferred;

"Alkylamino" refers to methylamino, ethylamino, propylamino, isopropylamino, n-butylamino, iso-butylamino, sec-butylamino, tert-butylamino, n-pentylamino, iso-pentylamino, tert-pentylamino, neo-pentylamino, 2-methylbutylamino, 1,2-dimethyl-propylamino, 1-ethyipropylamino, hexylamino and dimethylamino, diethylamino, dipropylamino, diisopropylamino, dibutylamino, diisobutylamino, where methylamino, ethylamino and dimethylamino, diethylamino are preferred;

"alkyl sulfide" refers to methylsulfide, ethylsulfide, propylsulfide, isopropylsulfide, n-butylsulfide, iso-butylsufide, sec-butysulfide, tert-butylsulfide, n-pentylsulfide, iso-pentyl sulfide, tert-pentylsulfide, neo-pentylsulfide, 2-methylbutylsulfide, 1,2-dimethyipropylsulfide, 1-ethyipropylsulfide, hexylsulfide, where methylsulfide and ethylsulfide are were preferred;

"Polar solvent" refers to the-solvents including ethyl acetate, 1,4-dioxane, acetone, t-butanol and so on;

"Nonprotonic polar solvent" refers to solvents including dimethyl sulfoxide, N, N-dimethyl formamide, dichloromethane, chloroform, tetrahydrofurane, 1,4-dioxane, 1,2-dimethyl glycol ether and so on;

"Protonic polar solvent" refers to solvents including methanol, ethanol, propanol, t-butanol and so on;

"Heating condition" refers to a temperature from above room temperature to reflux;

"Peroxydizing reagent" refers to reagents including m-chloroperoxybenzoate acid, t-peroxybutanol, peroxide hydrogen and so on;

The term "pharmaceutically acceptable salt" encompasses carboxylate salts having organic and inorganic cations, such as alkali and alkaline earth metal cations (for example, sodium, potassium, calcium, and aluminum), ammonium, or organic cations, (for example, methyl ammonium, ethyl ammonium, 2-hydroxyethyl animonium), and the like which can be obtained by reactions with acid organic acids which include propionic, oxalic, malonic, succinic, maleic, fumaric, lactic, malic, tartaric, citric, aspartic, glutamic acid and the like or the ammonium salts which can be obtained by reacting with lysine, arginine, omithine and then hydrochloric, hydrobromic, hydrofluoric, nitric, sulfuric, phosphoric, formic, acetic, picric, methanesulfonic, ethane sulfonic acid.

"Optical isomer" refers to compounds that include optically pure compounds and their mixture of enantiomers, diastereoisomers, optical isomers.

Triptolide derivatives, their pharmaceutically acceptable salts or optically active isomers of the invention may be made into a variety of therapeutic dosage forms which contain active components from 0.001 to 99.9% (weight) and appropriate pharmaceutically acceptable carriers for oral, parenteral and intestine administration.

All sorts of medical or pharmaceutical agents containing the effective dosage of triptolide derivatives of the present invention may be used on the treatment of the patient according to the age, health condition, the degree of severity and duration of the patients, administrative methods and individual drug sensitivity.

EXAMPLES

Figure 1:
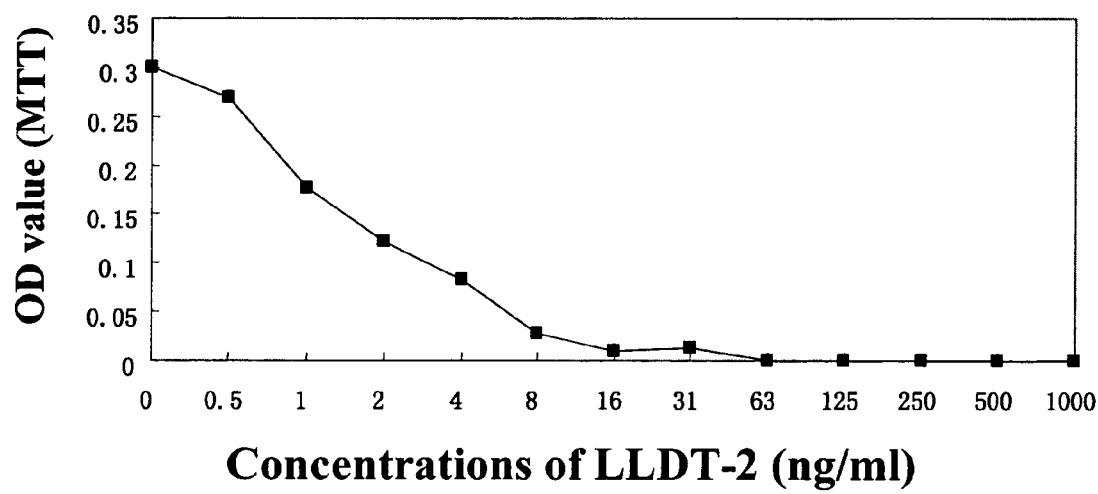
FIG. 1 shows the cytotoxicity of triptolide (LLDT-2) on lymphocyte.

The following examples are intended to illustrate but not in any way limit the invention.

Example 1

Preparation of (5R)-5-hydroxytriptonide

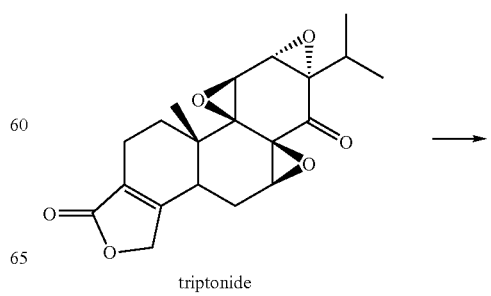

triptonide

-continued

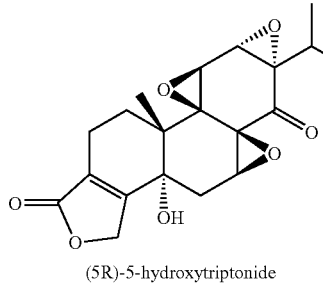

(5R)-5-hydroxytriptonide

-continued

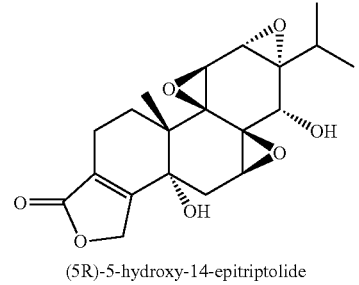

(5R)-5-hydroxy-14-epitriptolide

To a solution of triptonide (374 mg,1.04 mmol) in DMSO (20 ml) was added SeO$_2$ (461 mg, 4.16 mmol). The mixture was gently refluxed for 10 hours. Then the mixture was cooled down to room temperature, filtered through a short pad of silicon gel, rinsed with ethyl acetate. The solvent was removed under reduced pressure. Ethyl acetate and saturated Na$_2$CO$_3$ were added to the residue. After vigorous extraction, the organic layer was washed with water and brine, dried with anhydrous sodium sulfate. After concentration, the residue was purified by flash column chromatography to provide (5R)-5-hydroxytriptonide in 82% yield (319 mg, 0.85 mmol).

$^1$H NMR (DMSO-d$_6$, 400 MHz) δ 4.88 (m, 2H), 4.11 (d, J=2.9 Hz, 1H), 4.08 (d, J=2.9 Hz, 1H), 3.42 (d, J=4.4 Hz, 1H), 2.24 (sept, J=6.9 Hz, 1H), 1.96-2.20 (m, 4H), 1.83 (ddd, J=6.4, 11.7, 11.8 Hz, 1H), 1.08 (wide, dd, J=5.2, 12.4 Hz, 1H), 0.91 (s, 3H), 0.88 (d, J=6.9 Hz, 3H), 0.78 (d, J=6.9 Hz, 3H); $^{13}$C NMR (DMSO-d$_6$, 100 MHz) δ 198.4, 173.2, 161.9, 124.5, 69.9, 68.7, 65.1, 64.2, 61.0, 59.0, 58.7, 56.0, 29.7, 25.5, 24.2, 18.0, 16.8, 16.3, 16.0; IR (KBr) 3508, 2962, 1765, 1709, 1040 cm$^{-1}$; MS (EI, 70 eV) m/z 374 (M+, 9), 331 (35), 217 (43), 191 (50), 113 (100); mp 244-246° C. (dec.).

Example 2

Preparation of (5R)-5-hydroxytriptolide and (5R)-5-hydroxy-14-epitriptolide

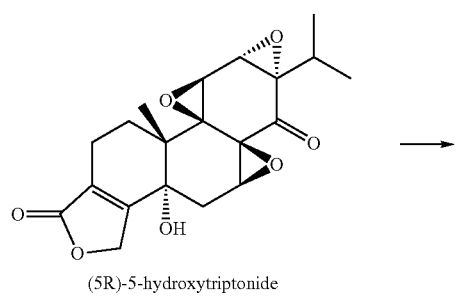

(5R)-5-hydroxytriptonide

To a suspension of (5R)-5-hydroxytriptolnide (20 mg, 0.053 mmol) in methanol (5 ml) was added NaBH$_4$ (8 mg, 0.21 mmol) at 0° C. The reaction was stirred for 2 hours and the mixture turned to a clear solution. After removal of the solvent under reduced pressure, the residue was diluted with ethyl acetate and washed with water and brine, dried with anhydrous sodium sulfate. After concentration, the residue was purified by flash column chromatography to provide to provide (5R)-5-hydroxytriptolide in 38% yield (7.5 mg, 0.02 mmol) and (5R)-5-hydroxy-14-epitriptolide in 56% yield (11.3 mg, 0.03 mmol) as white solids.

(5R)-5-hydroxytriptolide $^1$H NMR (DMSO-d$_6$, 400 Hz) δ 5.32 (s, 1H), 4.87 (m, 2H), 4.57 (br.s, 1H), 3.73 (d, J=2.9 Hz, 1H), 3.53 (d, J=2.9 Hz, 1H), 3.38 (s, 1H), 3.34 (d, J=5.0 Hz, 1H), 2.07-2.19 (m, 4H), 1.94-2.06 (m, 1H), 1.76 (ddd, J=6.4, 11.6, 11.9 Hz, 1H), 1.05 (dd, J=5.3, 12.4 Hz, 1H), 0.99 (s, 3H), 0.90 (d, J=6.9 Hz, 3H), 0.77 (d, J=6.9 Hz, 3H); $^{13}$C NMR (DMSO-d$_6$, 100 Hz) 173.2, 162.7, 124.1, 71.0, 69.7, 68.6, 63.9, 62.6, 61.4, 58.7, 55.9, 54.0, 30.3, 27.3, 23.1, 17.6, 16.8, 16.6, 16.3; IR (KBr) 3467, 2962, 1765, 1433, 1030 cm$^{-1}$; MS (EI, 70 eV) m/z 377 (M+1, 3), 343 (4), 329 (22), 287 (27), 163 (30), 71(47), 43 (100); mp 240-242° C. (dec.).

(5R)-5-hydroxy-14-epitriptolide $^1$H NMR (DMSO-d$_6$, 400 Hz) δ 5.32 (br.s, 1H), 4.89 (m, 2H), 4.14 (br.s, 1H), 3.72 (d, J=2.9 Hz, 1H), 3.58 (d, J=5.1 Hz, 1H), 3.45 (d, J=2.9 Hz, 1H), 2.23(sept, J=6.9 Hz, 1H), 1.99-2.19 (m, 4H), 1.79 (ddd, J=6.6, 11.7, 12.1 Hz, 1H), 1.07 (m, 1H), 0.99 (s, 3H), 0.97 (d, J=6.9 Hz, 3H), 0.70 (d, J=6.9 Hz, 3H); $^{13}$C NMR (DMSO-d$_6$, 100 Hz) δ 173.2, 162.8, 124.0, 69.6, 68.6, 65.5, 65.3, 63.8, 62.0, 56.5, 53.4, 52.1, 30.1, 26.7, 23.6, 19.0, 16.8, 16.2, 15.6; IR (KBr) 3458, 3392, 2955, 1751, 1030 cm$^{-1}$; MS (EI, 70 eV) m/z 376 (M$^+$, 8), 359 (41), 273 (46), 193 (55), 71 (100); mp 238-240° C. (dec.).

Example 3

Preparation of Δ$^{5,6}$-dehydrotriptonide

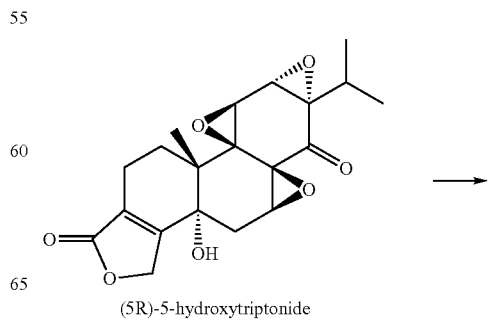

(5R)-5-hydroxytriptonide

-continued

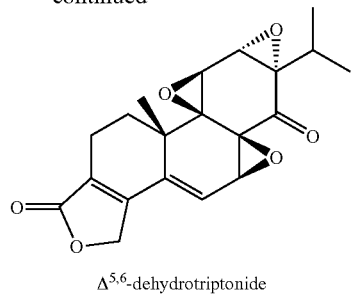

Δ[5,6]-dehydrotriptonide (5R)-5-hydroxytriptonide (224 mg, 0.60 mmol) was dissolved in dichloromethane (10 ml) combined with pyridine (4 ml, 50.57 mmol), then the mixture was added dropwise TFAA (600 mg, 2.85 mmol) and stirred for 12 hours. After removal of the solvent under reduced pressure, the residue was diluted with water, then extracted with ethyl acetate. The organic layer was washed with 1M $H_2SO_4$, saturated $NaHCO_3$, water and brine, dried with anhydrous sodium sulfate. After concentration, the residue was purified by flash column chromatography to provide Δ[5,6]-dehydrotriptonide in 75% yield (166 mg, 0.47 mmol).

$^1$H NMR (CDCl$_3$, 400 MHz) δ 6.01 (d, J=3.7 Hz, 1H), 4.90 (m, 2H), 4.01 (d, J=2.9 Hz, 1H), 3.84 (d, J=2.9 Hz, 1H), 3.47 (d, J=3.7 Hz, 1H), 2.46-2.51 (m, 1H), 2.44 (sept, J=6.9 Hz, 1H), 2.24-2.36 (m, 1H), 1.50 (d, J=3.7 Hz, 1H), 1.47-1.49(m, 1H), 1.31 (s, 3H), 0.99 (d, J=6.9 Hz, 3H), 0.89 (d, J=6.9 Hz, 3H); $^{13}$C NMR (CDCl$_3$, 100 MHz) δ 196.3, 172.7, 152.5, 141.0, 127.7, 120.0, 68.8, 66.3, 65.3, 64.5, 59.6, 56.5, 55.6, 37.1, 30.3, 25.6, 22.9, 18.0, 17.1, 16.3; IR (KBr) 3432, 2960, 2850, 1762, 1724, 1433, 1356, 1038 cm$^{-1}$; MS (EI, 70 eV) m/z 356 (M+, 21), 338 (31), 323 (43), 285 (87), 257 (89), 128 (96), 115 (100); mp 242-244° C. (dec).

Example 4

Preparation of (5R,6S)-5,6-epoxytriptonide

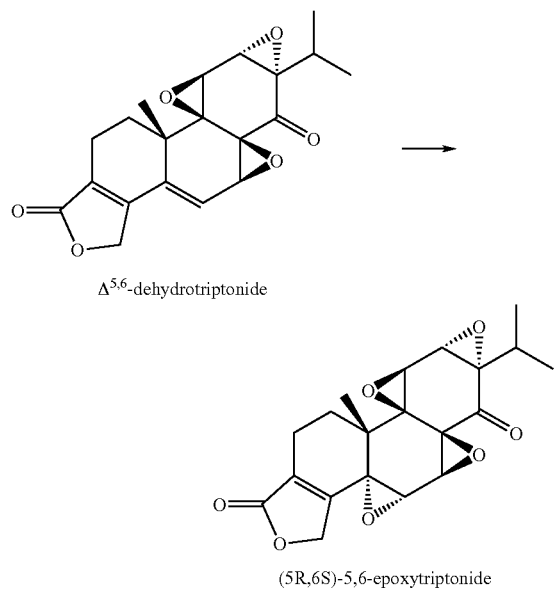

Δ[5,6]-dehydrotriptonide (5R,6S)-5,6-epoxytriptonide

To a solution of Δ[5,6]-dehydrotritonide (280 mg, 0.78 mmol) in dichloromethane (10 ml) was added mCPBA70- 75% (500 mg, 2.03 mmol), the reaction was refluxed for 6 hours, and quenched by adding 5% $Na_2S_2O_3$. The mixture was diluted with dichloromethane, and the aqueous phase was extracted with chloromethane. The combined organic layer washed with saturated $NaHCO_3$, water and brine, dried with anhydrous sodium sulfate. After concentration, the residue was purified by flash column chromatography to provide (5R,6S)-5,6-epoxytriptonide in 75% yield (220 mg, 0.59 mmol).

$^1$H NMR (CDCl$_3$, 400 MHz) δ 4.63 (m, 2H), 3.91 (d, J=2.9 Hz, 1H), 3.84 (d, J=2.9 Hz, 1H), 3.81(d, J=2.2 Hz, 1H), 3.62 (d, J=2.2 Hz, 1H), 2.47-2.52 (m, 1H), 2.38 (sept, J=6.9 Hz, 1H), 2.26-2.33 (m, 1H), 1.69 (dt, J=6.2, 12.0 Hz, 1H), 1.50-1.57 (m, 1H), 1.28 (s, 3H), 0.96 (d, J=6.9 Hz, 3H), 0.86 (d, J=6.9 Hz, 3H); $^{13}$C NMR (CDCl$_3$, 100 MHz) δ 195.5, 171.8, 153.9, 134.0, 67.8, 66.7, 63.1, 62.3, 60.3, 59.6, 58.1, 56.7, 55.8, 36.3, 27.3, 25.6, 17.9, 17.6, 17.5, 16.3; IR (KBr) 3446, 2966, 1766, 1732, 1431, 1229, 1038 cm$^{-1}$; MS (EI, 70 eV) m/z 372 (M+, 6), 357 (13), 329 (4), 231 (100), 203 (12), 187 (9); mp 252-254° C. (dec.).

Example 5

Preparation of cis-(5R,6S)-5,6-dihydroxtriptonide

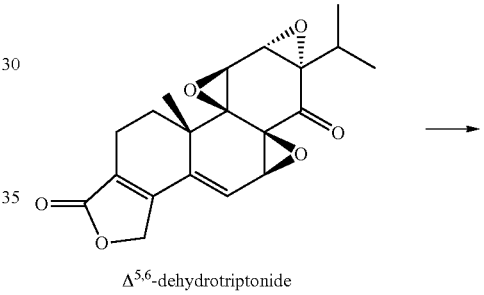

Δ[5,6]-dehydrotriptonide

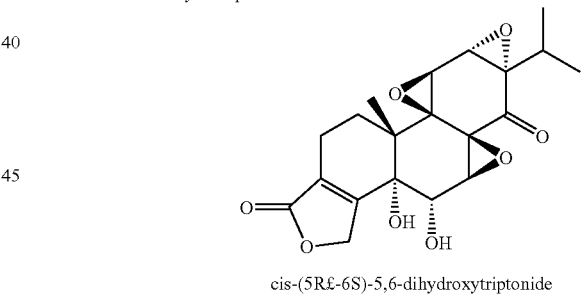

cis-(5R,6S)-5,6-dihydroxytriptonide

To a solution of Δ[5,6]-dehydrotritonide (72 mg, 0.20 mmol) in 3.2 ml 1,4-dioxane and 1.6 ml water was added $K_3Fe(CN)_6$ (250 mg, 0.76 mmol), $K_2CO_3$ (100 mg, 0.72 mmol) and $OsO_4$ (2.6 mg, 0.01 mmol). The mixture was stirred for 14 hours under room temperature and quenched by adding 2 ml saturated $Na_2SO_3$ solution. The reaction was neutralized to pH 7 with sulfuric acid, diluted by water, and extracted with ethyl acetate. The organic layer washed with saturated $NaHCO_3$, water and brine, dried with anhydrous sodium sulfate. After concentration, the residue was purified by flash column chromatography to provide cis-(5R,6S)-5,6-dihydroxytriptonide in 37% yield (29 mg, 0.07 mmol).

$^1$H NMR (DMSO-d$_6$, 400 MHz) δ 4.91 (m, 2H), 4.12 (d, J=2.9 Hz, 1H), 4.11(d, J=2.9 Hz, 1H), 4.01 (s, 1H), 3.15 (s, 1H), 2.23 (sept, J=6.9 Hz, 1H), 2.09-2.17 (m, 1H), 1.95-2.07 (m, 1H), 1.85 (dt, J=5.4, 11.9 Hz, 1H), 1.07 (dd, J=4.6, 12.1

Hz, 1H), 0.88 (s, 3H), 0.87 (d, J=6.9 Hz, 3H), 0.78 (d, J=6.9 Hz, 3H); $^{13}$C NMR (DMSO-$d_6$, 100 MHz) δ 197.7, 173.1, 160.4, 125.6, 72.6, 71.0, 65.7, 65.0, 64.6, 64.0, 61.4, 58.6, 56.0, 25.6, 24.8, 18.0, 16.8, 16.0, 15.7; IR (KBr) 3431, 2968, 1740, 1724, 1672, 1429, 1136, 1022 cm$^{-1}$; MS (EI, 70 eV) m/z 390 (M$^+$, 8), 372 (37), 361 (40), 343 (35), 179 (72), 167 (100), 113 (83); mp 266-268° C. (dec).

Example 6

Preparation of Δ$^{5,6}$-dehydrotriptolide and Δ$^{5,6}$-dehydro-14-epitriptolide

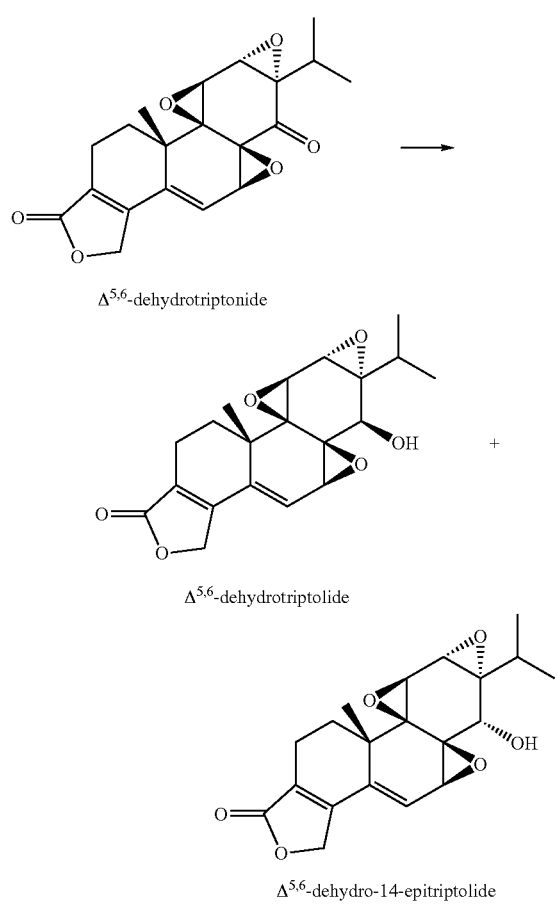

Δ$^{5,6}$-dehydrotriptonide

Δ$^{5,6}$-dehydrotriptolide

Δ$^{5,6}$-dehydro-14-epitriptolide

To a suspension of Δ$^{5,6}$-dehydrotriptonide (36 mg, 0.1 mmol) in methanol (3 ml) was added NaBH$_4$ (8 mg, 0.2 mmol) at 0° C. The reaction was stirred for 1 hour and the mixture turned to a clear solution. After removal of the solvent under reduced pressure, the residue was diluted with ethyl acetate and washed with water and brine, dried with anhydrous sodium sulfate. After concentration, the residue was purified by flash column chromatography to provide Δ$^{5,6}$-dehydrotriptolide in 50% yield (18 mg, 0.05 mmol) and Δ$^{5,6}$-dehydro-14-epitriptolide in 50% yield (18 mg, 0.05 mmol) as white solids.

Δ$^{5,6}$-dehydrotriptolide $^1$H NMR (CDCl$_3$, 400 MHz) δ 6.02 (d, J=3.9 Hz, 1H), 4.88 (m, 2H), 3.88 (d, J=3.3 Hz, 1H), 3.58 (d, J=1.0 Hz, 1H), 3.52 (d, J=3.3 Hz, 1H), 3.45 (d, J=3.9 Hz, 1H), 2.87 (d, J=11.0 Hz, 1H) 2.43-2.48 (m, 1H), 2.29-2.33 (m. 1H), 2.25 (sept, J=6.9 Hz, 1H), 1.36-1.49 (m, 2H), 1.34 (s, 3H), 1.03 (d, J=6.9 Hz, 3H), 0.90 (d, J=6.9 Hz, 3H); $^{13}$C NMR (CDCl$_3$, 100 MHz) δ 172.9 152.8, 140.0, 127.1, 121.5, 73.8, 68.8, 66.1, 65.1, 63.3, 57.6, 55.9, 55.0, 37.2, 29.7, 28.1, 22.5, 17.8, 17.0, 16.9; IR (KBr) 3626, 3473, 2968, 1776, 1749, 1655, 1416, 1040, 1024 cm$^{-1}$; MS (EI, 70 eV) m/z 358(M$^+$, 2), 343 (3), 325 (10), 299 (29), 269 (17), 245 (100), 128 (26); mp 194-196° C.

Δ$^{5,6}$-dehydro-14-epitriptolide $^1$H NMR (CDCl$_3$, 400 MHz) δ 6.07 (d, J=4.2 Hz, 1 Hz), 4.90 (m, 2H), 4.63 (d, J=3.0 Hz, 1H), 3.76 (d, J=4.8 Hz, 1H), 3.73 (d, J=3.1 Hz, 1H), 3.40 (d, J=3.1 Hz, 1H), 2.42-2.47 (m, 1H), 2.37 (sept, J=6.9 Hz, 1H), 2.22-2.34 (m, 1H), 1.93 (d, J=3.0 Hz, 1H), 1.34-1.49 (m, 2H), 1.31 (s, 3H), 1.11 (d, J=6.9 Hz, 3H), 0.83 (d, J=6.9 Hz, 3H); $^{13}$C NMR (CDCl$_3$, 100 MHz) δ 173.0, 153.1, 140.6, 127.0, 122.0, 68.9, 66.2, 65.7, 64.8, 64.4, 56.7, 53.2, 51.6, 37.4, 29.9, 27.4, 22.6, 19.0, 17.1, 15.8; IR (KBr) 3435, 2966, 1778, 1753, 1429, 1086 cm$^{-1}$; MS (EI, 70 eV) m/z 358 (M$^+$, 13), 343 (14), 329 (23), 315 (35), 257 (70), 192 (77), 97 (100); mp 172-174° C.

Example 7

Preparation of (5R,6S)-5,6-epoxytriptolide and (5R,6S)-5,6-epoxy-14-epitriptolide

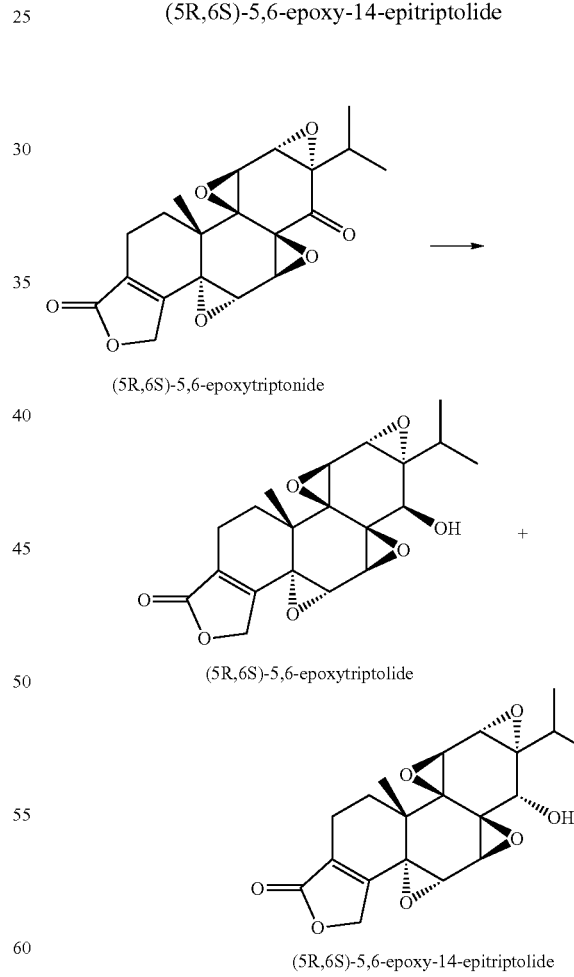

(5R,6S)-5,6-epoxytriptonide (5R,6S)-5,6-epoxytriptolide (5R,6S)-5,6-epoxy-14-epitriptolide To a suspension of (5R,6S)-5,6-epoxytriptonide (36 mg, 0.1 mmol) in methanol (3 ml) was added NaBH$_4$ (8 mg, 0.21 mmol) at 0° C. The reaction was stirred for 1 hour and the mixture turned to a clear solution, and was neutralized with sulfuric acid. After removal of the solvent under reduced pressure, the residue was diluted with ethyl acetate and washed with water and brine, dried with anhydrous sodium sulfate. After concentration, the residue was purified by flash column chromatography to provide (5R,6S)-5,6-epoxytriptolide in 56% yield (20 mg, 0.053 mmol) and (5R,6S)-5,6-epoxy-14-epitriptolide in 43% yield (16 mg, 0.043 mmol) as white solids.

(5R,6S)-5,6-epoxytriptolide $^1$H NMR (CDCl$_3$, 600 MHz) δ 4.62 (m, 2H), 3.80 (d, J=1.5 Hz, 1H), 3.79 (d, J=2.9 Hz, 1H), 3.59 (d, J=2.5 Hz, 1H), 3.51 (d, J=2.9 Hz, 1H), 3.41 (d, J=12.2 Hz, 1H), 2.78 (d, J=12.2 Hz, 1H), 2.45-2.49 (m, 1H), 2.28-2.33 (m, 1H), 2.20 (sept, J=6.9 Hz, 1H), 1.58-1.63 (m, 1H), 1.47-1.51 (m, 1H), 1.31 (s, 3H), 0.99 (d, J=6.9 Hz, 3H), 0.87 (d, J=6.9 Hz, 3H); $^{13}$C NMR (CDCl$_3$, 100 MHz) δ 172.0, 154.3, 133.9, 74.0, 67.9, 65.1, 64.2, 61.1, 59.8, 58.2, 57.6, 57.1, 55.0, 36.4, 28.0, 26.7, 17.7, 17.4, 16.9; IR (KBr) 3489, 2928, 1778, 1431, 1039 cm$^{-1}$; MS (EI, 70 eV) m/z 374 (M$^+$, 1), 358 (3), 329 (9), 257 (38), 231 (44), 71 (100); mp: 248-250° C. (dec).

(5R,6S)-5,6-epoxy-14-epitriptolide $^1$H NMR (CDCl$_3$, 400 MHz) δ 4.66 (m, 2H), 4.52 (d, J=2.9 Hz, 1H), 3.93 (d, J=2.6 Hz, 1H), 3.84 (d, J=2.6 Hz, 1H), 3.67 (d, J=3.1 Hz, 1H), 3.41 (d, J=3.1 Hz, 1H), 2.45-2.52 (m, 1H), 2.35 (sept, J=6.9 Hz, 1H), 2.24-2.32 (m, 1H), 1.80 (d, J=2.9 Hz, 1H), 1.61-1.67 (m, 1H), 1.49-1.53 (m, 1H), 1.28 (s, 3H), 1.08 (d, J=6.9 Hz, 3H), 0.81 (d, J=6.9 Hz, 3H); $^{13}$C NMR (CDCl$_3$, 100 MHz) δ 172.1, 154.7, 133.8, 67.9, 65.6, 65.5, 62.8, 62.2, 60.1, 57.8, 56.2, 53.8, 52.9, 36.6, 27.2, 26.9, 18.9, 17.5, 17.4, 15.7; IR (KBr) 3485, 2928, 1751, 1435, 1082, 1040 cm$^{-1}$; MS (EI, 70 eV) m/z 374 (M$^+$, 1), 358 (4), 345 (10), 327 (11), 257 (40), 231(98), 71 (100); mp 200-202° C. (dec).

Example 8

Preparation of cis-(5R,6S)-5,6-dihydroxytriptolide and cis-(5R,6S)-5,6-dihydroxy-14-epitriptolide

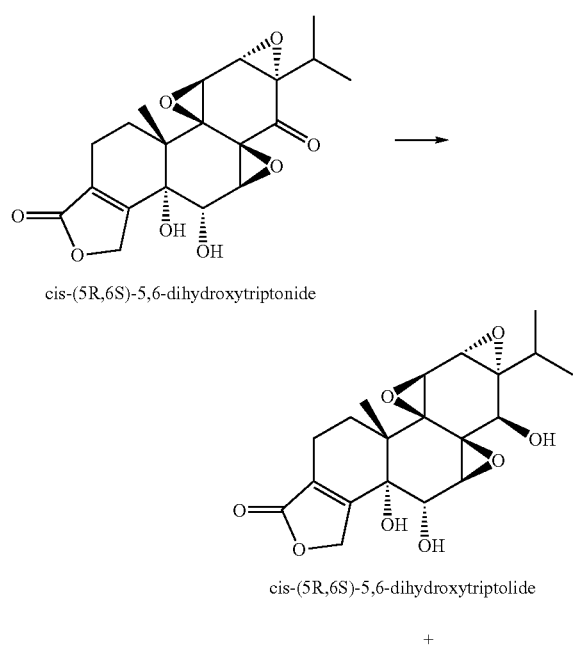

cis-(5R,6S)-5,6-dihydroxytriptonide cis-(5R,6S)-5,6-dihydroxytriptolide

+

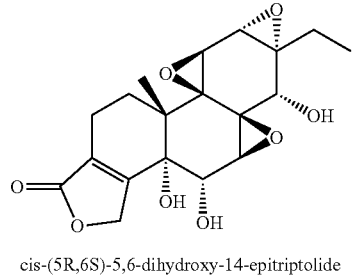

cis-(5R,6S)-5,6-dihydroxy-14-epitriptolide

To a suspension of cis-(5R,6S)-5,6-dihydroxytriptonide (39 mg, 0.1 mmol) in methanol (3 ml) was added NaBH$_4$ (8 mg, 0.21 mmol) at 0° C. The reaction was stirred for 1 hour and the mixture turned to a clear solution, and was neutralized with sulfuric acid. After removal of the solvent under reduced pressure, the residue was diluted with ethyl acetate and washed with water and brine, dried with anhydrous sodium sulfate. After concentration, the residue was purified by flash column chromatography to provide cis-(5R,6S)-5,6-dihydroxytriptolide in 25% yield (10 mg, 0.026 mmol) and cis-(5R,6S)-5,6-dihydroxy-14-epitriptolide in 75% yield (29 mg, 0.074 mmol) as white solids.

cis-(5R,6S)-5,6-dihydroxytriptolide $^1$H NMR (DMSO-d$_6$, 400 MHz) δ 4.90 (m, 2H), 3.96 (s, 1H), 3.75 (d, J=2.9 Hz, 1H), 3.52 (d, J=2.9 Hz, 1H), 3.39 (s, 1H), 3.14 (s, 1H), 2.16 (sept, J=6.9 Hz, 1H), 2.06-2.13 (m, 1H), 1.92-2.06 (m, 1H), 1.71-1.82 (m, 1H), 1.01-1.08 (m, 1H), 0.95 (s, 3H), 0.89 (d, J=6.9 Hz, 3H), 0.75 (d, J=6.9 Hz, 3H); $^{13}$C NMR (DMSO-d$_6$, 100 MHz) δ 173.2, 161.2, 125.3, 72.4, 70.8, 70.5, 66.3, 64.9, 63.9, 62.2, 62.1, 55.8, 53.9, 27.3, 23.7, 17.6, 16.9, 16.6, 15.7; IR (KBr) 3572, 3494, 3380, 2926, 1766, 1427, 1350, 1041, 1016 cm$^{-1}$; MS (EI, 70 eV) m/z 392 (M$^+$, 1), 377 (6), 374 (4), 359 (10), 349 (50), 303 (52), 167 (100), 71 (98); mp 232-234° C. (dec).

cis-(5R,6S)-5,6-dihydroxy-14-epitriptolide $^1$H NMR (DMSO-d$_6$, 400 MHz) δ 4.89 (m, 2H), 4.09 (s, 1H), 3.96 (s, 1H), 3.73 (d, J=2.9 Hz, 1H), 3.42 (d, J=2.9 Hz, 1H), 3.41 (s, 1H), 2.19 (sept, J=6.9 Hz, 1H), 2.06-2.11 (m, 1H), 1.93-2.03 (m, 1H), 1.76-1.81 (m, 1H), 0.99-1.03 (m, 1H), 0.95 (d, J=6.9 Hz, 3H), 0.94 (s, 3H), 0.68 (d, J=6.9 Hz, 3H); $^{13}$C NMR (DMSO-d$_6$, 100 MHz) δ 173.2, 161.4, 125.2, 72.4, 70.8, 66.3, 65.4, 63.5, 62.8, 59.7, 56.6, 52.3, 26.9, 24.2, 19.1, 17.0, 15.6; IR (KBr) 3504, 2962, 1714, 1444, 1242, 1053 cm$^{-1}$; MS (EI, 70 eV) m/z 392 (M$^+$, 1), 374 (2), 349 (13), 303 (14), 257 (11), 179 (44), 91 (95), 71 (100); mp 246-248° C. (dec).

BIOLOGICAL ACTIVITY TESTING EXPERIMENT

In the following experiments, LLDT-8 was presented by Department of Medicinal Chemistry (Shanghai Institute of Materia Medica, Shanghai Institutes for Biological Sciences, Chinese Academy of Sciences) and is >99% pure. LLDT-8 is composed of white amorphous powder. The parent compound of LLDT-8, LLDT-2 was also used as control.

Animals: Inbred Balb/c mice, ICR mice and KM mice, 6-8 weeks of age, male SD rat, 130-160 g weight, were provided by Shanghai Experimental Animal Center of Chinese Academy of Sciences (Certificate No 99-003). C57BL/6 mice were bred by Animal Facility of Shanghai Institute of Materia Medica. DBA/1 mice were from Japan, and bred by Animal Facility of Shanghai Institute of Materia Medica. The mice were housed in specific pathogen free (SPF) conditions with room temperature of $(24\pm2)°$ C., 12-h light/dark cycle, and provided with sterile food and water ad libitum.

Reagents:

*Mycobacterium tuberculosis* was purchased from The Shanghai Institute of Biological Products (200109001).

Bovine type II collagen (0418N) was purchased from Collagen Research Center (Tokyo, Japan).

Cyclosporin A injection was from Novartis (143MFD0600).

Con A (Concanavalin A), LPS (*Escherichia coli* 055:B5), and DMSO were Sigma products.

Sac (*Staphylococcus aureus* Cowan strain 1) was from Pansorbina cells, Biosciences, Inc (La Jolla, Calif. 92039, USA).

RPMI-1640 and fetal bovine serum (FBS) were obtained from Gibco.

[$^3$H]thymidine was from Shanghai Institute of Nuclear Research.

Experiment 1

MTT Cytotoxic Assay

Method:

Mice were sacrificed by cervical dislocation, and spleens were collected under sterile conditions then teased through a nylon mesh. Erythrocytes were lysed. Cells were washed and resuspended at $5\times10^6$/ml in RPMI-1640 media supplemented with 10% FBS.

For one 96 well plate assay, 90 µl of cells, 45 µl of sample and 45 µl of RPMI-1640 media with 10% FBS were added into each well with the final volume 180 µl. The negative control wells (containing 90 µl of RPMI-1640 media with 10% FBS and 90 pt of cells), blank control (180 µl of RPMI-1640 media with 10% FBS) were also performed. Incubate plate for 48 hours at 37° C., 5% $CO_2$ in a humidified incubator. 18 µl of MTT solution (5 mg/ml) was added for 6-7 h.

90 µl of MTT lysis solution was added to each well followed by a further incubation at 37° C. for 6-7 h. And the absorbance was measured at 570 nm using a plate reader.

Result:

The $IC_{50}$ value (concentration required to reduce the viability of cells by 50% as compared with the control cells) for LLDT-2 (FW=360) is 0.74 ng/ml (R=0.991) or 2 nM (FIG. 1).

Figure 2:
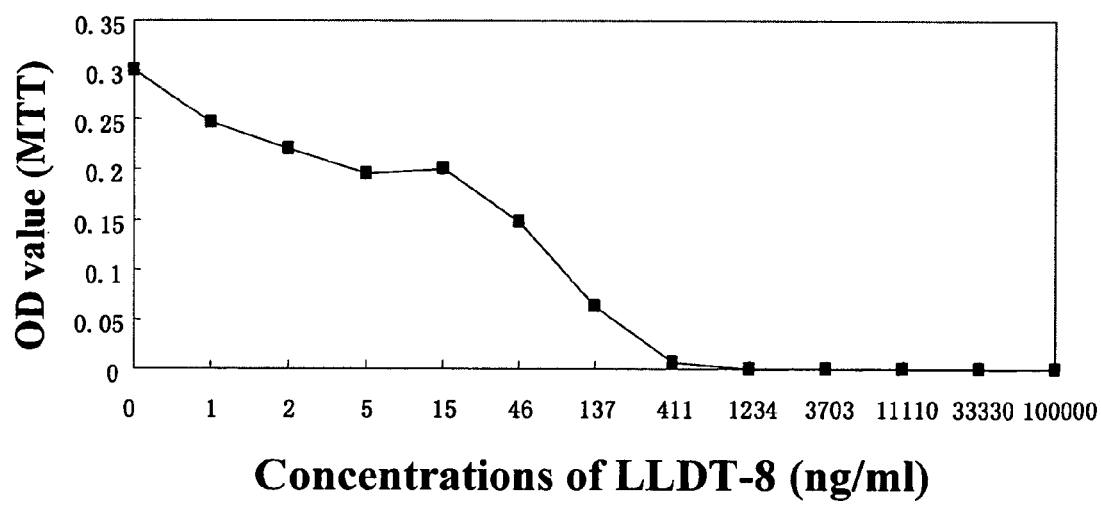
FIG. 2 shows the cytotoxicity of (5R)-5-hydroxytriptolide (LLDT-8) on lymphocyte.

The $IC_{50}$ value for LLDT-8 (FW=376) is 78.2 ng/ml (R=0.983) or 208 nM (FIG. 2).

Statistical analysis: GraphPHD InPlot. Nonlinear Regression Analysis.

Experiment 2

Effect on ConA and LPS Induced T- and B-lymphocyte Proliferation

Method:

Mice were sacrificed by cervical dislocation, and spleens were collected under sterile conditions then teased through a nylon mesh. Erythrocytes were lysed. Cells were washed and resuspended at $5\times10^6$/ml in RPMI-1640 media containing 10% FBS. For one 96 well plate assay, 100 pt of cells, 50 µl of sample and 50 µl of ConA/LPS were added into each well with the final volume 200 µl. The control wells were set up with 50 µl of RPMI-1640 media instead of ConA/LPS.

Plates were incubated for 48 h (ConA) or 60 h (LPS), respectively, at 37° C., 5% $CO_2$ in a humidified incubator. In the last 8 h of incubation, 25 µl $(1.9\times10^{10}$ Bq) of [$^3$H]thymidine was added. After plates were incubated for 48 h, the plates (ConA) were stored at −20° C., then after another 12 h, the plates (LPS) were stored at −20° C.

At the end of incubation, pulsed cells were harvested on a glass filter using a cell harvester (HARVESTER96®, TOMTEC) and allowed to dry. Incorporation of radioactive thymidine was determined by using liquid Scintillation and Luminescence Counters (MicroBeta Trilux®, PerkinElmer).

Figure 3:
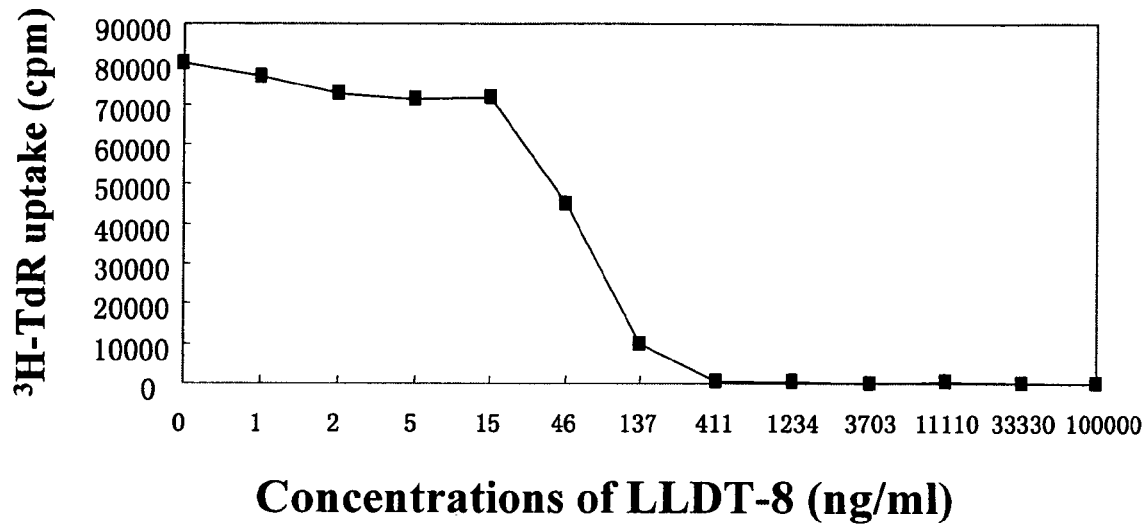
FIG. 3 shows that LLDT-8 inhibited ConA induced T-lymphocyte proliferation.
Figure 4:
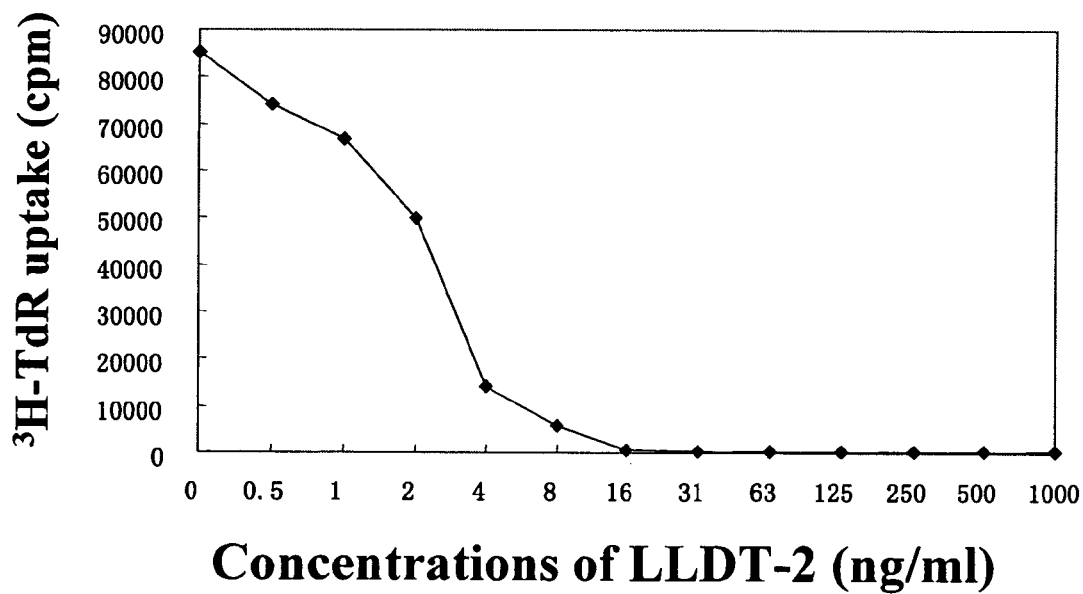
FIG. 4 shows that LLDT-2 inhibited ConA induced T-lymphocyte proliferation.
Figure 5:
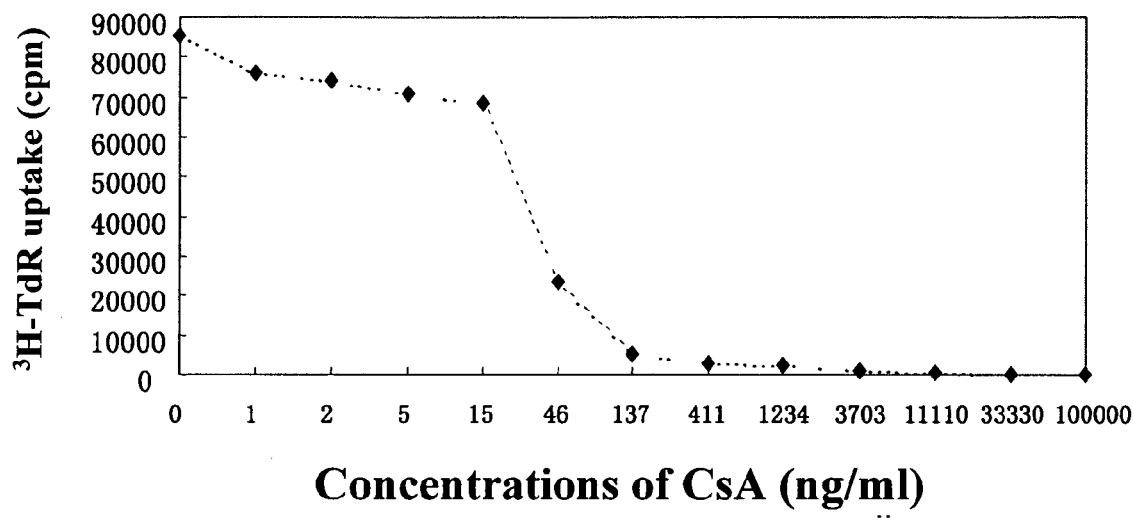
FIG. 5 shows that CsA inhibited ConA induced T-lymphocyte proliferation.

Result:

The results showed that the compounds strongly inhibited the proliferation of spleen cells induced either by ConA or LPS. The $ED_{50}$ of LLDT-8 for inhibiting T lymphocyte proliferation induced by ConA is 58.12 ng/ml or 154.6 nM (R=0.998) (FIG. 3), much lower than its $IC_{50}$ (200 nM); The $ED_{50}$ of LLDT-2 for inhibiting T lymphocyte proliferation is 2.44 ng/ml or 6.8 nM (R=0.998) (FIG. 4), much higher than its $IC_{50}$ (2 nM). Which implied that LLDT-8 is a more potent inhibitor in the T lymphocytes proliferative responses than its parent compound LLDT-2. Comparing with classical immunosuppressant Cyclosporine (CsA) in clinic, the inhibitory activity of LLDT-8 is much weaker (about 5.4 fold). The $ED_{50}$ of CsA (FW=1202.6) is 34.62 ng/ml or 28.8 nM (R=0.998) (FIG. 5).

Figure 6:
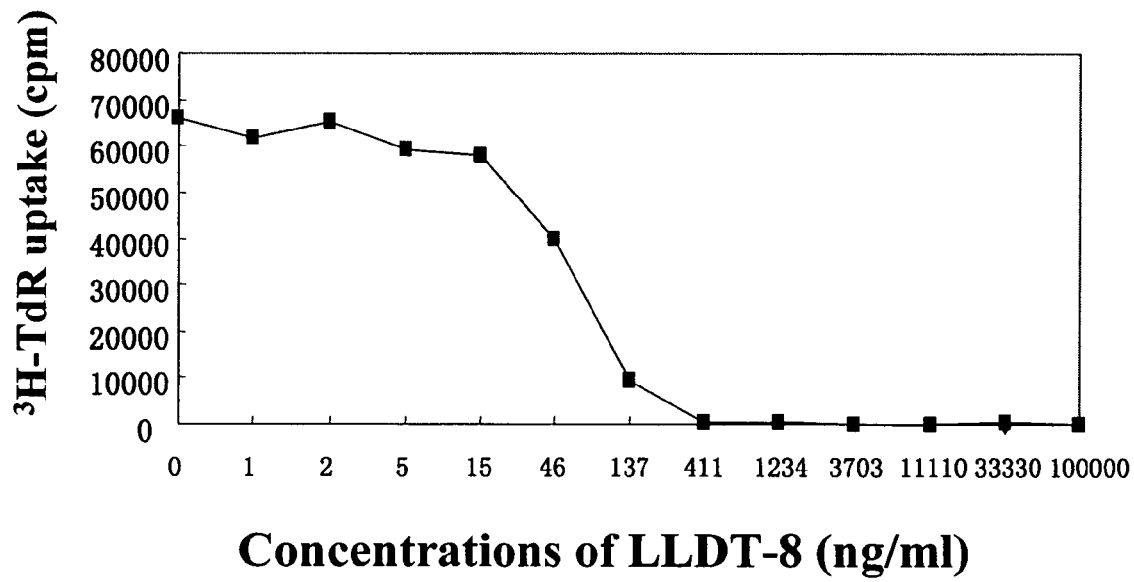
FIG. 6 shows that LLDT-8 inhibits LPS induced B-lymphocyte proliferation.
Figure 7:
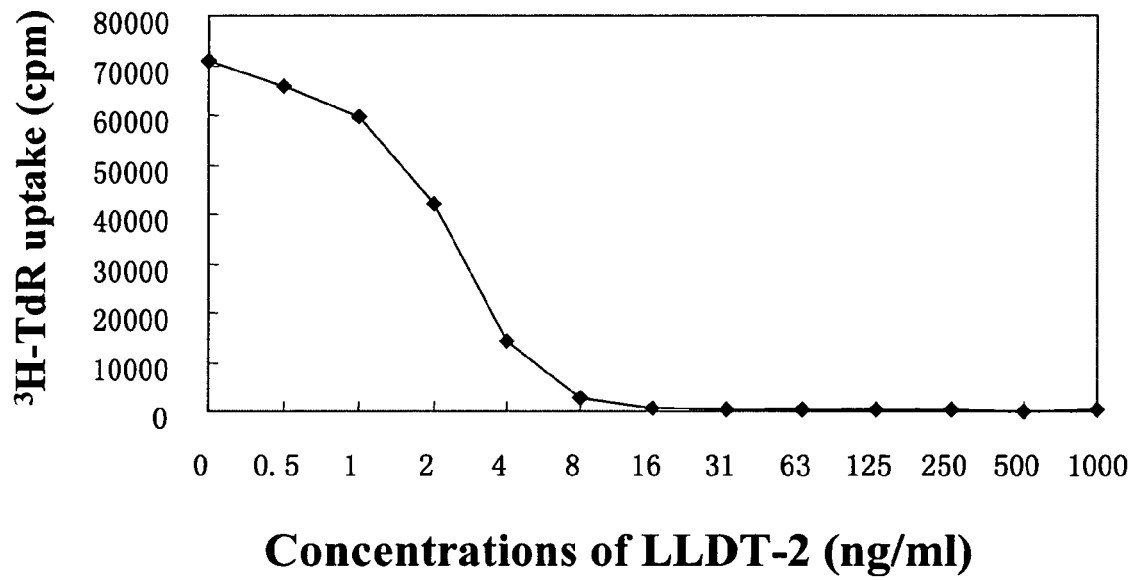
FIG. 7 shows LLDT-2 inhibited LPS induced B-lymphocyte proliferation.
Figure 8:
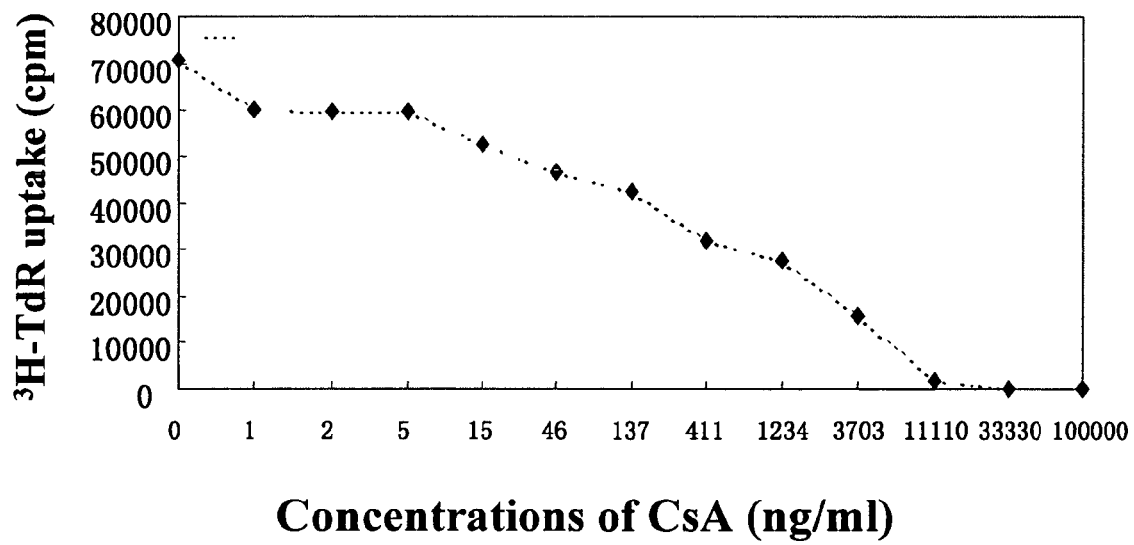
FIG. 8 shows CsA inhibited LPS induced B-lymphocyte proliferation.

The $ED_{50}$ of LLDT-8 for inhibiting B lymphocyte proliferation induced by LPS is 59.80 ng/ml or 159 nM (R=0.998) (FIG. 6), much lower than its $IC_{50}$ (200 nM); The $ED_{50}$ of LLDT-2 for inhibiting B lymphocyte proliferation is 2.38 ng/ml or 6.6 nM (R=0.998) (FIG. 7), much higher than its $IC_{50}$ (2 mM). Which implied that LLDT-8 is a more potent inhibitor of the B lymphocyte proliferative responses than its parent compound LLDT-2. Comparing with CsA, LLDT-8 also showed more potent inhibitory activity on B lymphocyte proliferation induced by LPS (about 4.3 fold). The $ED_{50}$ of CsA (FW=1202.6) is 816.7 ng/ml or 679 nM (R=0.989) (FIG. 8).

The results confirmed that present LLDT-2 had potent immunosuppressive activity, while significant cytotoxicity limits its broad use.

Table 1 summarized the results of cytotoxicity and lymphocyte proliferation assay for a series of compounds.

TABLE 1

The immunobioactivity of derivatives of triptolide.

| Compounds | Concentration (M) | Cytotoxicity OD Value | Lymphocyte Proliferation (cpm) | |
|---|---|---|---|---|
| | | | T cell | B cell |
| Control | — | 0.337 | 125789 | 87373 |
| LLDT-15 | $10^{-8}$ | 0.327 | 69613 | 77139 |
| | $10^{-7}$ | 0.316 | 63914 | 85240 |
| | $10^{-6}$ | 0.156 | 10296 | 30889 |
| LLDT-16 | $10^{-8}$ | 0.372 | 89029 | 71877 |
| | $10^{-7}$ | 0.337 | 75599 | 82285 |
| | $10^{-6}$ | 0.304 | 76204 | 80768 |
| LLDT-17 | $10^{-8}$ | 0.334 | 74069 | 73969 |
| | $10^{-7}$ | 0.355 | 67561 | 76376 |
| | $10^{-6}$ | 0.310 | 84825 | 82861 |
| LLDT-18 | $10^{-8}$ | 0.367 | 92807 | 79808 |
| | $10^{-7}$ | 0.295 | 53513 | 75147 |
| | $10^{-6}$ | 0.039 | 462 | 833 |

TABLE 1-continued

The immunobioactivity of derivatives of triptolide.

| Compounds | Concentration (M) | Cytotoxicity OD Value | Lymphocyte Proliferation (cpm) | |
|---|---|---|---|---|
| | | | T cell | B cell |
| LLDT-19 | $10^{-8}$ | 0.346 | 76183 | 69690 |
| | $10^{-7}$ | 0.340 | 71177 | 70587 |
| | $10^{-6}$ | 0.340 | 79418 | 82989 |
| LLDT-20 | $10^{-8}$ | 0.374 | 69785 | 78259 |
| | $10^{-7}$ | 0.350 | 54771 | 85145 |
| | $10^{-6}$ | 0.263 | 25344 | 63169 |
| LLDT-21 | $10^{-8}$ | 0.359 | 83465 | 76181 |
| | $10^{-7}$ | 0.332 | 73513 | 75766 |
| | $10^{-6}$ | 0.361 | 97217 | 86610 |
| LLDT-22 | $10^{-8}$ | 0.374 | 64367 | 84748 |
| | $10^{-7}$ | 0.345 | 68787 | 89706 |
| | $10^{-6}$ | 0.157 | 2662 | 16807 |
| LLDT-23 | $10^{-8}$ | 0.366 | 84713 | 76993 |
| | $10^{-7}$ | 0.349 | 104791 | 86481 |
| | $10^{-6}$ | 0.302 | 55614 | 99672 |

Experiment 3

Effect on MLR Response

Method:

C57BL/6 and Balb/c mice were sacrificed by cervical dislocation, and spleens were collected under sterile conditions then teased through a nylon mesh. Erythrocytes were lysed. Cells were washed and resuspended at $6\times10^6$/ml in RPMI-1640 media with 10% FBS.

Splenocytes from responder (C57BL/6) were mixed with stimulator (Balb/c), which was pretreated with $^{60}$Co Gamma Ray irradiation (3000 rads).

Stimulator and responder cells were cultured in a 200 µl volume in 96-well plate in the presence of drugs or medium, at 37° C., 5% $CO_2$ in a humidified incubator, for 3, 4, and 5 days, respectively. In the last 8 h of incubation, cells were treated with 25 µl ($3.8\times10^{10}$ Bq) of [$^3$H]Thymidine.

At the end of incubation, pulsed cells were harvested on a glass filter using a cell harvester (HARVESTER96®, TOMTEC) and allowed to dry. Incorporation of radioactive thymidine was determined by using liquid Scintillation and Luminescence Counters (MicroBeta Trilux®, PerkinElmer).

Result:

LLDT-8 strongly inhibited MLR response of C57BL/6 against Balb/c, the potency is much higher than CsA (about 2.5-fold).

Figure 9:
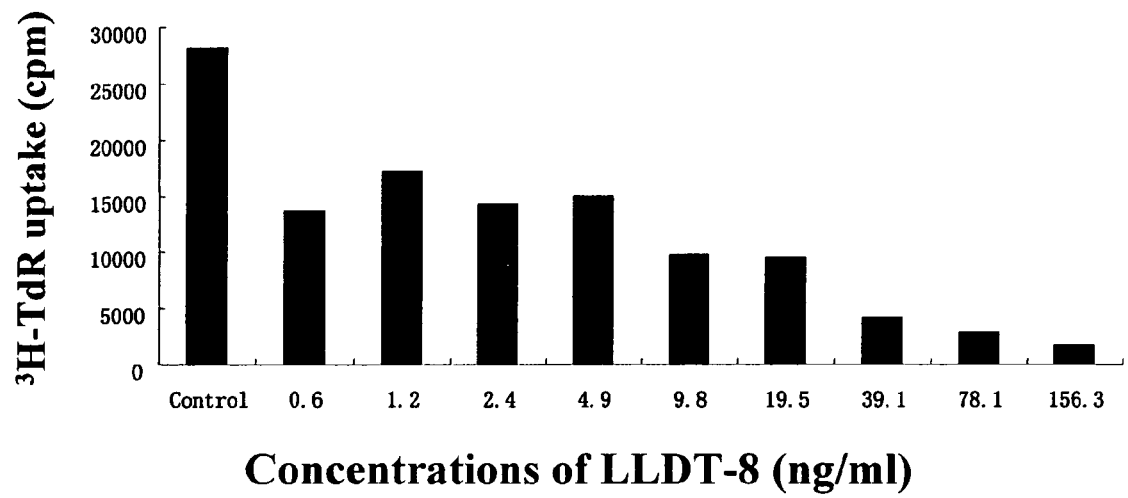
FIG. 9 shows LLDT-8 inhibited MLR response of C57BL/6 against Balb/c.
Figure 10:
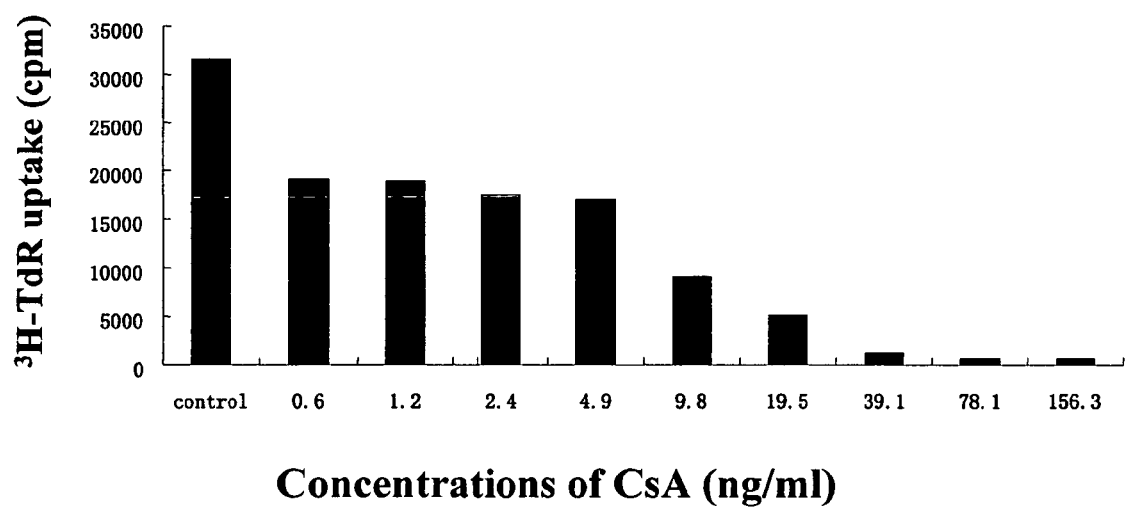
FIG. 10 shows CsA inhibited MLR response of C57BL/6 against Balb/c.

The $ED_{50}$ of LLDT-8 is 0.6 ng/ml (1.6 nM) (FIG. 9); the $ED_{50}$ of CsA is 4.9 ng/ml (4.1 nM) (FIG. 10).

Experiment 4

Effect on Cytokine Production

Method:

Mice were sacrificed by cervical dislocation, and spleens were collected under sterile conditions then teased through a nylon mesh. Erythrocytes were lysed. Cells were washed and resuspended at $5\times10^6$/ml in RPMI-1640 media with 10% FBS.

1 ml of spleen cells were treated with or without ConA (5 µg/ml) or Sac (1:10000) and in the presence or absence of drugs in a final volume of 2 ml.

After 24 h culture at 37° C., 5% $CO_2$ in a humidified incubator, cell-free supernatant was collected and frozen at −20° C. for ELISA.

IL-2, IL-12p40, IL-10, and IFN-γ levels were determined by Enzyme Linked Immuno Sorbance Assay (ELISA). TMB was taken as the enzyme substrate. The absorbance was measured at 450/570 nm by BioRad microplate reader. The amount of cytokines in sample supernatants were calculated based on standard curve using standard murine cytokines (rIL-2, rIL-12, rIL-10, and rIFN-γ).

Results:

LLDT-8 showed inhibitory effects on the production of T lymphocyte-derived IFN-γ (the effect is potent) and IL-2. The IL-12, TNF-α and IL-6 production from macrophage was also suppressed, while macrophage-derived IL-10 was promoted. It is obvious that LLDT-8 preferentially stimulates Th2 type cytokines production, while suppresses Th1 type cytokines production. Therefore, LLDT-8 has inhibitory effects on cell-mediated immune responses.

LLDT-8 strongly reduced Sac-stimulated IFN-γ production from murine spleen lymphocytes at the concentrations far below the $IC_{50}$ value for lymphocyte cytotoxicity. For example, this inhibitory effect could be observed even at the concentration of 0.01 nM (Table 2).

TABLE 2

LLDT-8 inhibited IFN-γ production from Sac-stimulated lymphocytes

| Concentration of LLDT-8 | IFN-γ production by lymphocytes stimulated with Sac | |
|---|---|---|
| (nM) | Mean Value (pg/ml) | SD |
| — | 1302.6 | 18.18 |
| 100 | 227.4 | 14.91 |
| 10 | 465.3 | 10.74 |
| 1 | 810.3 | 57.03 |
| 0.1 | 850.5 | 0 |
| 0.01 | 809.7 | 28.50 |

LLDT-8 suppressed ConA-induced IL-2 production from T lymphocytes (Table 3).

TABLE 3

LLDT-8 inhibited LL-2 production from ConA-stimulated lymphocytes

| Concentration of LLDT-8 | IL-2 production by lymphocytes stimulated with ConA | |
|---|---|---|
| (nM) | Mean Value (pg/ml) | SD |
| — | 3724.4 | 139.2 |
| 30 | 2872.7 | 24.7 |
| 3 | 3494.2 | 16.5 |
| 0.3 | 3857.2 | 172.5 |

LLDT-8 decreased the production of IL-12, TNF-α and IL-6, but increased IL-10 production from Sac-activated lymphocytes (Table 4).

TABLE 4

Effect of LLDT-8 on the cytokine productions from Sac-stimulated lymphocytes

| Concentration of LLDT-8 (nM) | Cytokine production by lyphocytes stimulated with Sac (pg/ml) | | | |
|---|---|---|---|---|
| | IL-10 | IL-12 | TNF-α | IL-6 |
| — | 2306 | 980 | 4062 | 1528 |
| 30 | 3262 | 602 | 3649 | 989 |
| 3 | 2816 | 939 | 3899 | 1403 |
| 0.3 | 2866 | 917 | 4686 | 1585 |

Experiment 5

The induction of T lymphocyte apoptosis

Method:
(1) The Tuf-tainer (non-adherent to cells) was pretreated with culture medium for 2 h;
(2) As that described in proliferation assay, Balb/c mice were sacrificed and their spleens were removed aseptically. A single cell suspension was prepared and resuspended in RPMI-1640 media at $5\times10^6$/ml.
(3) Cells were added to 5 μg/ml ConA or medium;
(4) The cells were cultured in 5% $CO_2$ incubator at 37° C. for 24-96 h;
(5) Cells were collected and washed with PBS, centrifugated at 400 g for 10 min at 4° C.;
(6) The collected cells were shaken 10 s violently and 1 ml ice-cold 70% ethanol was added dropwise, capped and fixed overnight at 40° C.;
(7) The cells were centrifuged at 3000 rpm for 5 min and the ethanol was removed; Incubated cells with 1 ml PI staining buffer at room temperature more than 30 min; FACs analysis was performed with 24 h.

Results:
The results indicated that LLDT-8 induced the apoptosis of murine T lymphocytes at the concentration below or near the $IC_{50}$ concentration for lymphocyte cytotoxicity, and reduced $CD4^+$ and $CD8^+$ T lymphocytes percentage, which offered mechanisms involved in the anti-inflammatory and immune suppressive activities.

Experiment 6

LLDT-8 Inhibited DNFB-induced Mouse Delayed Type Hypersensitivity Response (DTH)

Method:
Female Balb/c mice (age of 6-8 wk) were randomly divided into groups and immunized with 20 μl 0.5% DNFB solution in absolute acetone-olive oil (4:1) on each hind foot on day 0 and 1;
7-9 days after the initial immunization, mice were boosted with 10 μl 0.4% DNFB on both sides of the left ear, whereas the right ear was treated with vehicle alone;
Compounds were administered intraperitoneally (i.p.) or orally (p.o.) to the mice 1 h before DNFB booster immunization and 12 h later.
Ear swelling and other indexes were assessed 24-48 h after booster immunization.
Note: Female ICR mice (age of 6-8 wk) were immunized with 0.7% DNFB solution and boosted with 0.6% DNFB solution.

Results:
LLDT-8 was tested to confirm whether it has immunosuppressive effect on cell-mediated immune responses on the classical animal model of DNFB-induced mouse delayed type hypersensitivity response (DTH). The results indicated that LLDT-8 showed a very potent inhibitory effect on DTH when i.p. or p.o. administered to mice.

1. Intraperitoneal administration of LLDT-8 inhibited DTH response:

LLDT-8 significantly suppressed DNFB-induced mouse DTH when intraperitoneally administered to mice at the dose of 1 mg/Kg/d for 5 days. The potency of inhibitory effect was even higher than that of Cyclosporin A (10 mg/Kg). There was no obvious influence on lymph organs (spleen) and body weight in DTH mice when treated with LLDT-8 at the dose of 1 mg/Kg/d (Table 5).

TABLE 5

LLDT-8 inhibited DNFB-induced mouse DTH response (i.p.)

| Groups | Dosage (mg/kg) | Left ear (mg) | Right ear (mg) | Ear swelling (mg) | Body weight before/after i.p. (g) | Spleen (mg) |
|---|---|---|---|---|---|---|
| Control | — | 63.8 | 31.2 | 32.6 | 20/20 | 142.4 |
| CsA | 10 | 59.0 | 32.3 | 26.7 | 21/20 | 152.3 |
| LLDT-8 | 1 | 56.9 | 35.5 | 21.4 | 21/21 | 140.3 |

LLDT-8 treatment with medication change (in type, the dosage and frequency): 1 mg/Kg, 0.2 mg/Kg and 0.04 mg/Kg, once a day for 2 days, still exerted suppressive effects, to the same level as that of CsA (10 mg/Kg) (Table 6).

TABLE 6

LLDT-8 inhibited DNFB-induced mouse DTH response (i.p.)

| Groups | Dosage (mg/kg) | Left ear (mg) | Right ear (mg) | Ear swelling (mg) |
|---|---|---|---|---|
| Control | — | 61.1 | 30.0 | 31.1 |
| CsA | 10 | 55.6 | 32.5 | 23.1 |
| LLDT-8 | 1 | 56.4 | 33.0 | 23.4 |
| LLDT-8 | 0.2 | 55.3 | 37.4 | 17.9 |
| LLDT-8 | 0.04 | 55.5 | 29.4 | 26.1 |

ICR mice, n=5

It seemed that LLDT-8 exerted stronger immunosuppressive effect at the lower dosage. LLDT-8 treatment at 2 μg/Kg still inhibited the DTH response significantly (Table 7).

TABLE 7

LLDT-8 inhibited DNFB-induced mouse DTH response (i.p. at low dosages)

| Groups | Dosage (mg/kg) | Left ear (mg) | Right ear (mg) | Ear swelling $\bar{X} \pm SD$ (mg) |
|---|---|---|---|---|
| Control | — | 49.6 | 26.3 | 23.3 ± 4.3 |
| LLDT-8 | 200 | 44.3 | 27.2 | 17.1 ± 5.1* |
| LLDT-8 | 40 | 42.6 | 25.7 | 16.9 ± 2.7** |
| LLDT-8 | 8 | 46.3 | 29.7 | 16.6 ± 4.1** |
| LLDT-8 | 2 | 44.3 | 27.5 | 16.8 ± 5.4** |

Compared with control group, *$p < 0.05$, **$p < 0.01$;
Balb/c mice, n = 12

Lower concentration of LLDT-8 at the dose of 0.4 μg/Kg still markedly inhibits the DTH response, to the same level as those of CTX at 1 mg/Kg and LLDT-2 at 40 μg/Kg (Table 8).

TABLE 8

LLDT-8 inhibited DNFB-induced mouse DTH response (i.p. at lower dosages)

| Groups | Dosage (mg/kg) | Left ear (mg) | Right ear (mg) | Ear swelling $\overline{X} \pm SD$ (mg) | Body weight (g) before/after i.p. | Spleen (mg) |
|---|---|---|---|---|---|---|
| Control | — | 49.1 | 26.4 | 22.7 ± 2.1 | 22.4/21.9 | 154.0 |
| CTX | 1000 | 45.9 | 30.3 | 15.6 ± 8.1* | 22.1/21.1 | 141.2 |
| LLDT-2 | 40 | 47.9 | 30.2 | 17.7 ± 5.7 | 21.5/21.2 | 151.4 |
| LLDT-8 | 40 | 46.7 | 29.6 | 17.1 ± 4.9** | 21.6/21.4 | 168.5 |
| LLDT-8 | 4 | 42.1 | 26.8 | 15.3 ± 4.7** | 21.4/21.8 | 163.3 |
| LLDT-8 | 0.4 | 47.0 | 29.2 | 17.7 ± 4.7* | 22.3/22.6 | 164.2 |

Compared with control group, *$p < 0.05$, **$p < 0.01$;
Balb/c mice, n = 10

2. Oral administration of LLDT-8 inhibited DTH response:

Oral administration of LLDT-8 at 1 mg/Kg/d for 2 days remarkably suppressed the DNFB-induced mouse DTI response, which is a cell-mediated immune reaction (Table 9).

TABLE 9

LLDT-8 inhibited DNFB-induced mouse DTH response (p.o.)

| Groups | Dosage (mg/kg) | Left ear (mg) | Right ear (mg) | Ear swelling (mg) | Body weight (g) before/after i.p. | Spleen (mg) |
|---|---|---|---|---|---|---|
| Control | — | 49.3 | 25.9 | 23.4 | 20/19 | 125.8 |
| CsA | 10 | 33.4 | 25.7 | 7.7 | 20/18 | 123.0 |
| LLDT-2 | 0.2 | 41.2 | 24.5 | 16.7 | 21/20 | 127.0 |
| LLDT-8 | 1 | 40.4 | 27.3 | 13.1 | 21/21 | 124.4 |

Balb/c mice, n = 5-6

Low dosage of LLDT-8 showed significant inhibitory effect on DTH when orally administered. The immunosuppressive activity of LLDT-8 at 40 µg/Kg is equivalent to that of CsA at 4 mg/Kg (Table 10).

TABLE 10

LLDT-8 inhibited DNFB-induced mouse DTH response (p.o.)

| Groups | Dosage (mg/kg) | Left ear (mg) | Right ear (mg) | Ear swelling (mg) |
|---|---|---|---|---|
| Control | — | 75.2 | 33.7 | 41.5 |
| CsA | 4 | 72.5 | 39.8 | 32.7 |
| LLDT-8 | 1 | 63.5 | 39.4 | 24.1 |
| LLDT-8 | 0.2 | 68.2 | 38.2 | 30.0 |
| LLDT-8 | 0.04 | 69.0 | 35.2 | 33.8 |

ICR mice, n = 5-6

Experiment 7

LLDT-8 Inhibited the Production of Mouse B Lymphocyte Anti-sheep Red Blood Cell Specific Antibody Method:

Fresh sheep red blood cells (SRBC) were washed 3 times with PBS (pH 7.2), and diluted at 1:20 in sterile saline;

Fresh guinea pig serum was diluted at 1:10 in sterile saline;

Prepared mouse spleen cell suspension at $2 \times 10^7$/ml was provided;

The diluted SRBC, guinea pig serum, and cell suspension were mixed at 1 ml: 1 ml: 1 ml at 37° C. for 1.5 h; following centrifugation, the supernatants were collected and the absorbance at 520 nm was measured by spectrophotometry.

Mice were immunized after they were administered with different compounds for 3 days: SRBC were diluted at 5% ratio following washing 3 times with sterile saline. Each mouse was injected 0.2 ml of this diluted SRBC. On the 6th day after the immunization, mice were sacrificed and spleen cells were taken for the determination of antibody production.

Results:

The results suggest that LLDT-8 exhibit inhibitory effects not only on cell-mediated immune responses, but also on humoral-mediated immune responses. LLDT-8 markedly reduced B cell anti-SRBC specific antibody production, which was still significant at the low dosage of 40 µg/Kg (i.p. administration); CsA inhibited T cell functions almost without inhibition on B cell anti-SRBC antibody production; LLDT-8, as well as CsA, decreased the concentration of serum total IgG; treatment with LLDT-8 (i.p. administration) significantly increased the complement C3 level in serum, improved immune complexes clearance, which is a characteristics for most immunosuppressants, like CsA (Table 11).

TABLE 11

LLDT-8 inhibited anti-SRBC specific antibodies production by B lymphocytes (i.p.)

| Groups | Dosage (mg/kg) | QHS OD value | Total IgG (µg/10 µl) | C3 (µg/10 µl) | Body weight (g) | Spleen (mg/10 g) | Thymus (mg) |
|---|---|---|---|---|---|---|---|
| Control | — | 0.208 | 185.5 | 16.8 | 23.5 | 66.4 | 39.6 |
| CsA | 4 | 0.247 | 173.9 | 19.1 | 22.9 | 65.6 | 31.8 |
| LLDT-8 | 1 | 0.158 | 182.9 | 19.4 | 22.3 | 59.6 | 36.6 |
| LLDT-8 | 0.2 | 0.162 | 165.9 | 19.7 | 23.1 | 76.3 | 36.9 |
| LLDT-8 | 0.04 | 0.175 | 176.6 | 19.5 | 23.0 | 74.8 | 32.1 |

ICR mice, female, age of 6-8 wk, 8 mice/group, i.p. 4 times;
QHS is a assay developed from PFC.

The results also showed lower dosage of LLDT-8 (40 μg/Kg) was effective on the reduction of B cell anti-SRBC specific antibodies level with no significant effect on serum total IgG and complement C3 levels (Table 12).

TABLE 12

LLDT-8 inhibited anti-SRBC specific antibodies production by B lymphocytes (p.o.)

| Groups | Dosage (mg/kg) | QHS OD value | Total IgG (μg/10 μl) | C3 (μg/10 μl) | Body weight (g) | Spleen (mg/10 g) | Thymus (mg) |
|---|---|---|---|---|---|---|---|
| Control | — | 0.38 | 117 | 7.9 | 23.4 | 55.7 | 28.8 |
| CTX | 4 | 0.12 | 101 | 7.5 | 22.6 | 50.7 | 28.2 |
| LLDT-8 | 1 | 0.24 | 118 | 6.8 | 23.0 | 63.7 | 32.5 |
| LLDT-8 | 0.2 | 0.34 | 116 | 7.9 | 24.0 | 61.6 | 36.6 |
| LLDT-8 | 0.04 | 0.23 | 123 | 6.7 | 23.0 | 69.0 | 28.7 |

ICR mice, female, age of 6-8 wk, 8 mice/group, p.o. 4 times;
The positive control: CTX, i.p.

Experiment 8

Effect on Rat Adjuvant Arthritis

1. Induction of rat adjuvant arthritis (AA) and drug prevention

SD rats were immunized on day 0 by intradermal injection of Complete Freund's adjuvant (CFA), containing 10 mg heat-inactivated BCG in 1 ml paraffin oil, into the left hind paw in 0.1 ml for each rat. Right hind paw volume was determined before immunization (basic value, day 0) and repeated every 4 days from day 12. The polyarthritis severity was graded on a scale of 0-4: 0=no swelling; 1=isolated phalanx joint involvement; 2=involvement of phalanx joint and digits; 3=involvement of the entire region down to the ankle; 4=involvement of entire paw, including ankle. The maximum joint score was 16 for each rat.

The rats with AA were divided randomly into five groups which were LLDT-8 (3, 1, and 0.2 mg/Kg/d), CsA (10 mg/Kg/d) and AA model group (equal amount of vehicle.) given intraperitoneally from day −2 to day 28 after immunization.

Lymphocyte proliferation assay: Splenocytes were prepared aseptically from AA rat at day 28 and resuspended in RPMI-1640 medium supplemented with 10% fetal bovine serum.

$5 \times 10^5$ cells each well were inoculated into 96-well plate with ConA or LPS in a final volume of 200 μl. Cells were cultured in 5% $CO_2$ incubator at 37° C. for 48 h. Cells were pulsed with $1.9 \times 10^{10}$ Bq/well of [$^3$H]-thymidine 7-8 h before harvest. After the culture finished, cells were harvested onto glass fiber filters and the incorporated radioactivity was counted by a Beta Scintillator (MicroBeta Trilux, PerkinElmer Life Sciences).

Induction of cytokine production from splenocytes: For splenocyte cytokine production assay, $5 \times 10^6$ cells per well were cultured with or without ConA (5 μg/ml) in a final volume of 2 ml. After 24 h or 48 h culture, cell-free supernatant was collected and frozen at −20° C. for ELISA.

Preparation of peritoneal macrophages from AA rat and induction of cytokines: Peritoneal cells were harvested from AA rat at day 28 after immunization. The collected cells were washed with RPMI-1640 medium and the adherent cells were used as resident peritoneal macrophages. Peritoneal cells were cultured in RPMI-1640 medium with LPS (5 μg/ml) in 5% $CO_2$ incubator at 37° C. After 6, 24, 48 h culture, cell-free supernatant was collected and frozen at −20° C. for ELISA.

Figure 11:
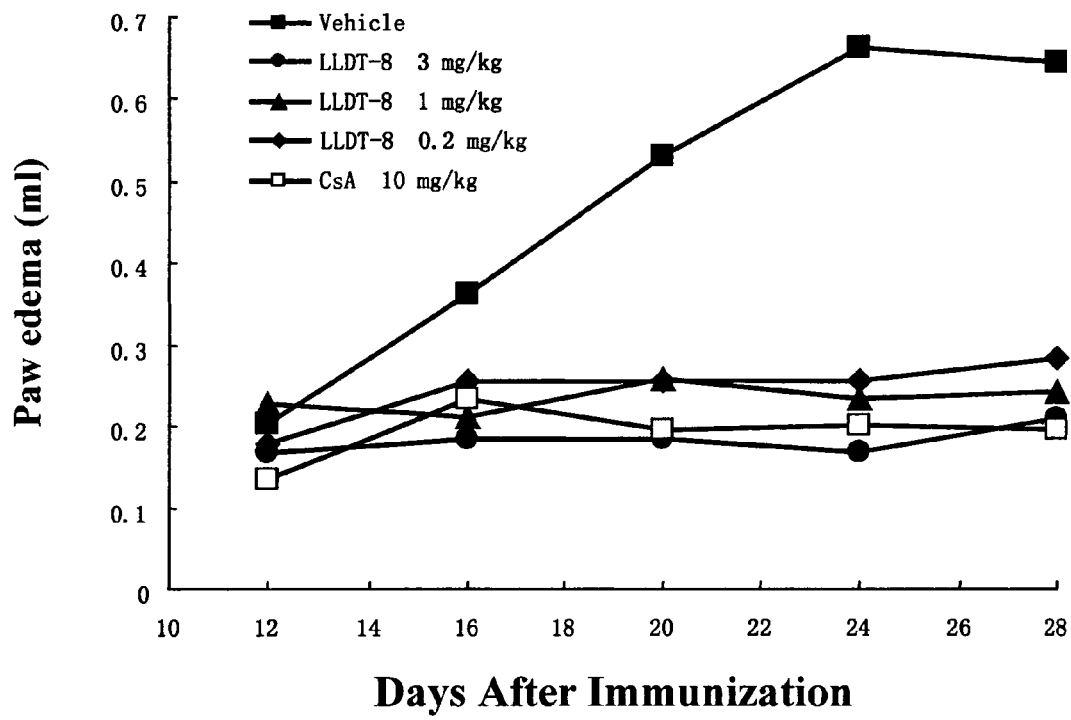
FIG. 11 shows the preventive effect of LLDT-8 on paw swelling in rats with adjuvant arthritis.
Figure 12:
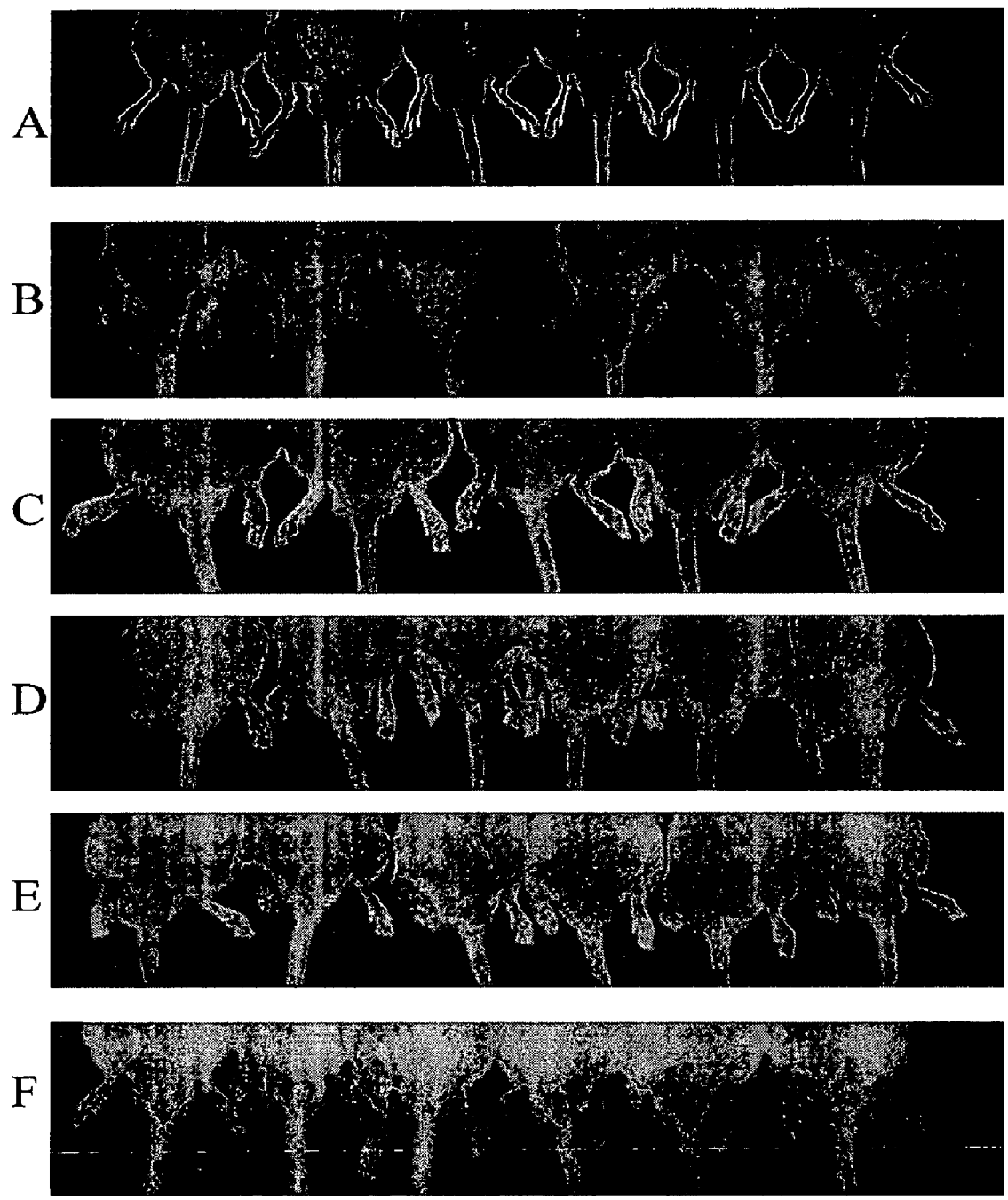
FIG. 12 shows the preventive effect of LLDT-8 on adjuvant arthritis of rats. In the figure, A) control; B) adjuvant arthritis; C)-E) LLDT-8: 3 mg/kg, 1 mg/kg, 0.2 mg/kg; F) CsA10 mg/kg.

Result:

LLTD-8 showed preventive effect on paw swelling in rats with adjuvant arthritis. Treatment with LLDT-8 (3, 1, and 0.2 mg/Kg/d) or CsA (10 mg/Kg/d) diminished the right hind paw swelling and polyarthritic symptoms after immunization. The inhibitory potency of LLDT-8 was at the same level with CsA (FIG. 11 and FIG. 12).

Compared with AA model group, AA model treated with LLDT-8 or CsA showed marked decrease of immune cell infiltration, smaller degree of synovial tissue proliferation, and less cartilage erosion.

Figure 13:
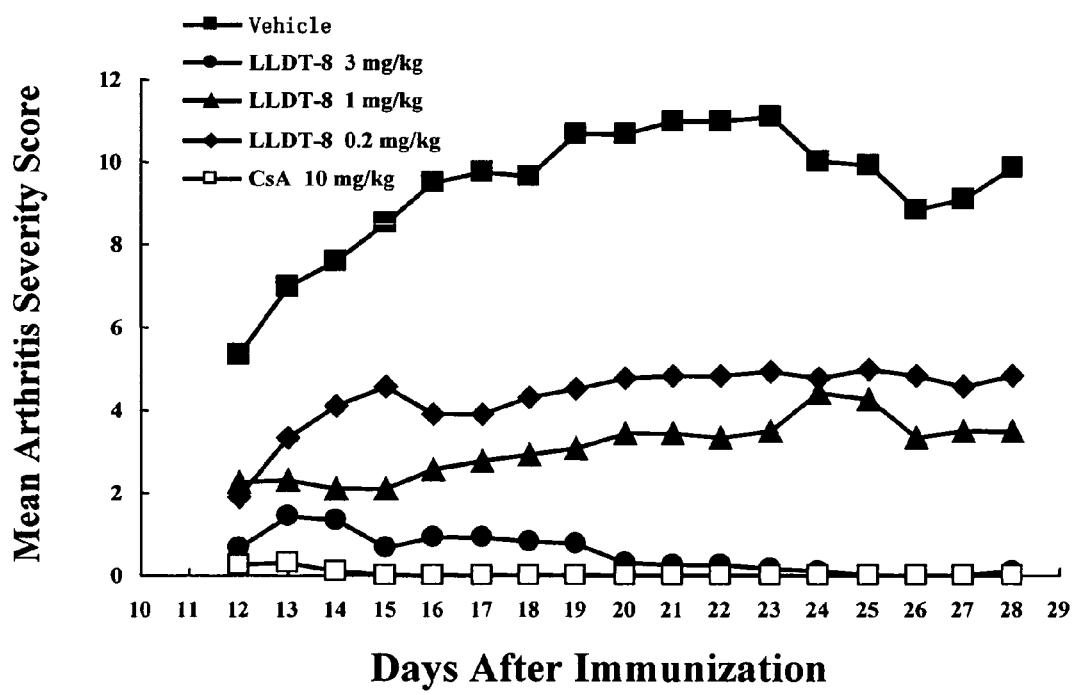
FIG. 13 shows the preventive effect of LLDT-8 on established polyarthritis of rats.

Assessment of polyarthritis severity showed the amelioration of established polyarthritis by treatment with LLDT-8 and CsA. (FIG. 13)

Figure 14:
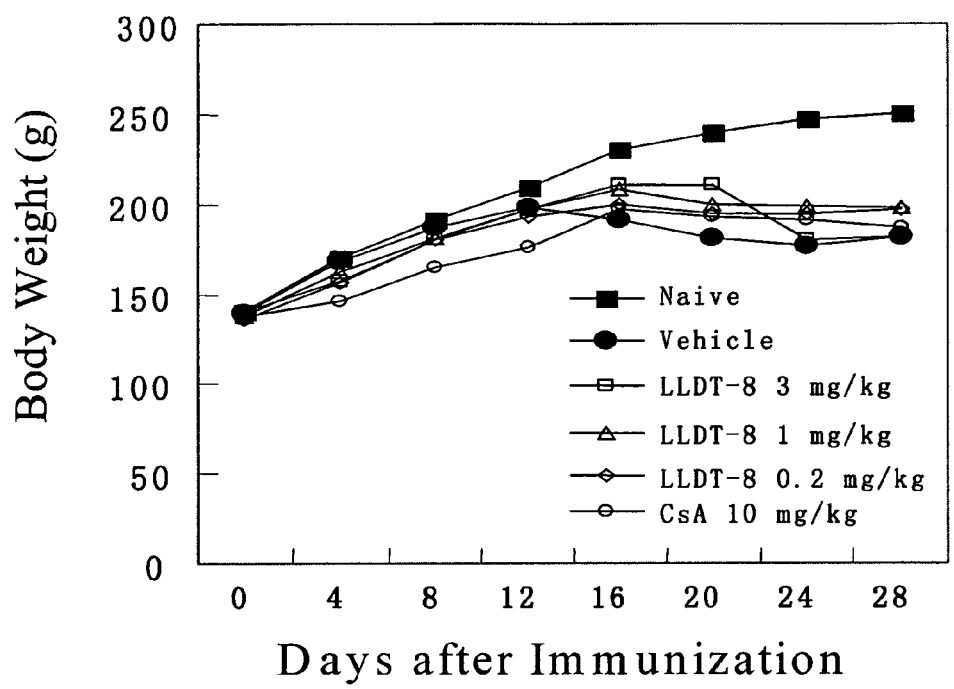
FIG. 14 shows the abrogation of body weight decrease in AA rat by treatment of LLDT-8.

Furthermore, the abrogation of body weight decrease in AA rat during the course of experiment was also shown in LLDT-8 treatment groups, including 3, 1, and 0.2 mg/Kg/d group, as well as 10 mg/Kg/d CsA treatment. (FIG. 14)

Figure 15:
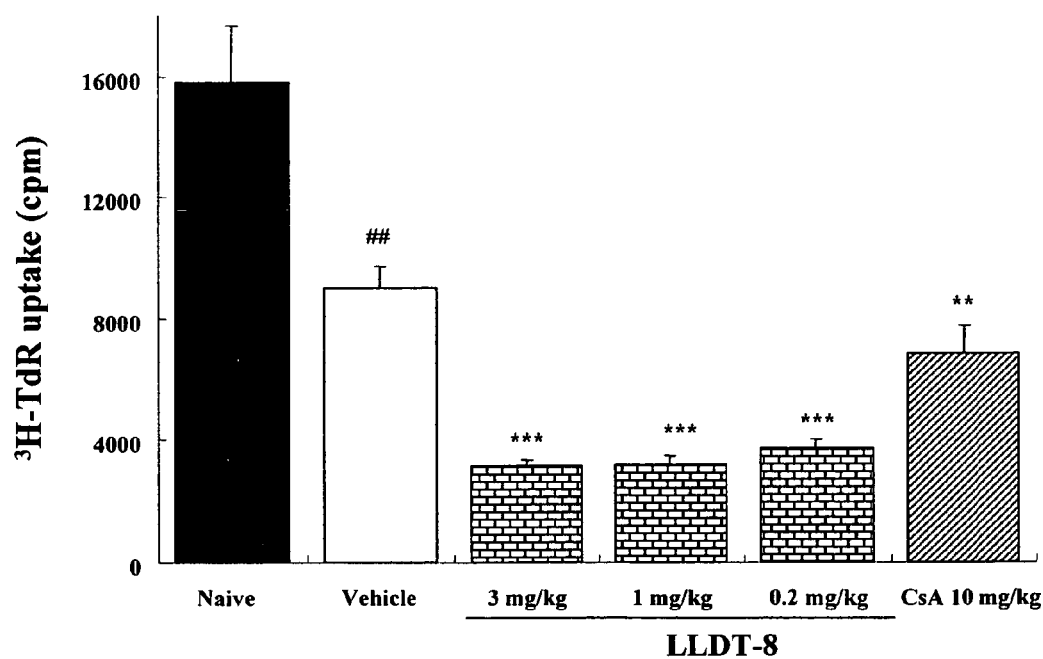
FIG. 15 shows LLDT-8 inhibited the proliferation of B splenocytes induced by LPS.

LLDT-8 inhibited the proliferation of B splenocytes induced by LPS (FIG. 15).

2. Therapeutic effect on rat adjuvant arthritis (AA)

Rats were immunized on day 0 by intradermal injection of Complete Freund's adjuvant (CFA), containing 10 mg heat-inactivated BCG in 1 ml paraffin oil, into the left hind paw in 0.1 ml for each rat. Inflammatory polyarthritis was induced in all immunized rats. Swelling in left paw and polyarthritic symptoms were seen from day 1, lasted for 4 days, and then diminished. Swelling in the same paw occurred again from day 8, reached the peak at day 16. The secondary symptoms, including the right hind paw swelling and polyarthritis, were seen from day 12. The polyarthritis severity was graded on a scale of 0-4: 0=no swelling; 1=isolated phalanx joint involvement; 2=involvement of phalanx joint and digits; 3=involvement of the entire region down to the ankle; 4=involvement of entire paw, including ankle.

Figure 16:
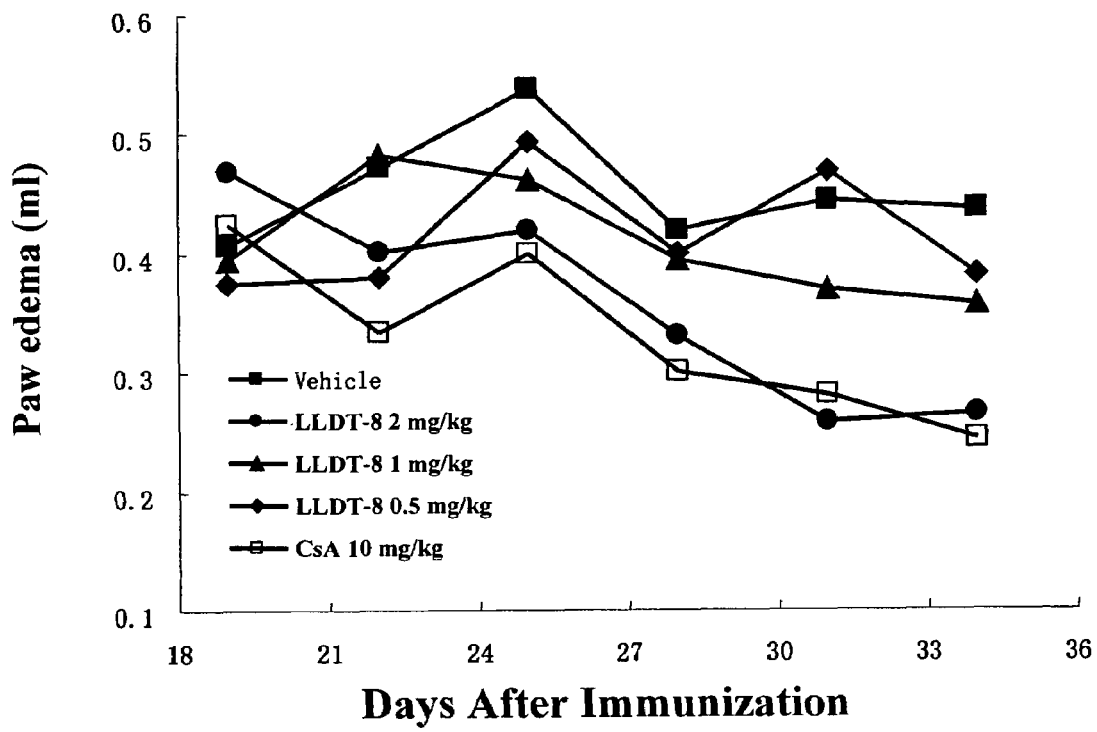
FIG. 16 shows the therapeutic effect of LLDT-8 on rat adjuvant arthritis (AA)
Figure 17:
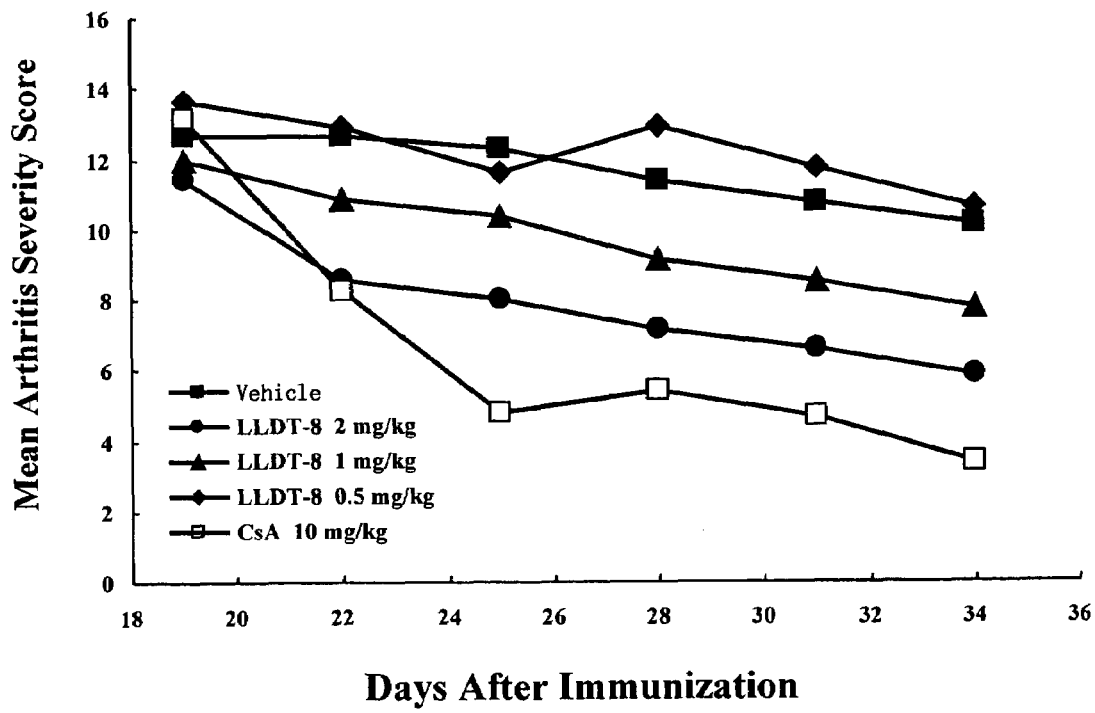
FIG. 17 shows the therapeutic effect of LLDT-8 on established polyarthritis of rats.

The rats with AA were divided randomly into 6 groups on day 19: including LLDT-8 (2 μl, 0.5 and 0.25 mg/Kg/d), CsA (10 mg/Kg/d) and AA model group (equal amount of vehicle) given intraperitoneally for 14 days. Right hind paw volume was determined before immunization (basic value, day 0) and repeated every 3 days. Animals were sacrificed on day 15, and thymus and spleen were harvested for thymus and spleen index assessment. Result: The secondary symptoms were established when the right hind paw severely swelled 19 days after adjuvant injection. LLDT-8 administration effectively cured the polyarthritic symptoms. Comparing with AA model rat, LLDT-8 treatment, especially at dose of 2 mg/Kg/d, markedly withdrew the symptoms (FIG. 16 and FIG. 17).

Experiment 9

Effect on Collagen-induced Arthritis in DBA/1 Mice

Method:

1. Induction and assessment of collagen-induced arthritis in DBA/1 mice

Bovine type II collagen was dissolved in 0.1 M acetic acid one day before experiment. DBA/1 mice were immunized at the tail base with 125 mg of collagen emulsified in CFA containing *Mycobacterium tuberculosis* strain H37Rv and boosted 3 weeks later. Mice were intraperitoneally treated with LLDT-8, starting 1 day before booster immunization and continuing for 2 weeks. The severity of arthritis was graded visually and expressed using the arthritic index. The arthritic score of each mouse was obtained by scoring each limb as severity 0 to 4 and taken the sum of the scores of the four limbs.

2. Splenocyte proliferation assay:

a. Peripheral lymph node cells and splenocytes were prepared aseptically from DBA/1 mice and suspended in RPMI-1640 medium supplemented with 10% fetal bovine serum.

b. Cells ($5 \times 10^6$ in 100 μl per well) were inoculated with or without 100 μl collagen in 96-well plate, and cultured in 5% $CO_2$ incubator at 37° C. for 3, 4 and 5 d, respectively. Cells were pulsed with 25 μl ($1.9 \times 10^{10}$ Bq/well) [$^3$H]-thymidine 24 h before harvest.

c. After the culture finished, culture plates were stored at −20° C.

d. Cells were collected onto glass fiber filters by harvester (HARVESTER96®, TOMTEC), and the incorporated radioactivity was counted by a Beta Scintillator (MicroBeta Trilux, PerkinElmer, Life Sciences) to present proliferation.

3. Anti-collagen specific antibody assay (ELISA)

a. Coating: Add collagen (50 mg/ml), 50 μl per well, to an ELISA plate and incubate for 1 h at 37° C. Wash the plate 3 times with PBS.

b. Standards and Samples: Add standards and samples, 50 μl per well. Cover the plate and incubate for 1 h at room temperature. Wash the plate 3 times with PBS.

c. HRP-linked Detection Antibody: Add rabbit anti-mouse IgG (H+L) coupled to HRP (1:2000) in blocking buffer, 5 μl, per well. Cover the plate and incubate at room temperature for 30 min. Wash the plate 3 times with PBS.

d. Substrate and Develop: Add citric acid+TMB+$H_2O_2$, 100 μl per well, and allow to develop at room temperature for 15 min.

e. Stop: Add 1M $H_2SO_4$ Solution, 50 μl per well, to stop reaction. The absorbance was measured at 450/570 nm.

f. Calculate: Determine the amount of antibody in each sample by reference to the standard curve.

Figure 18:
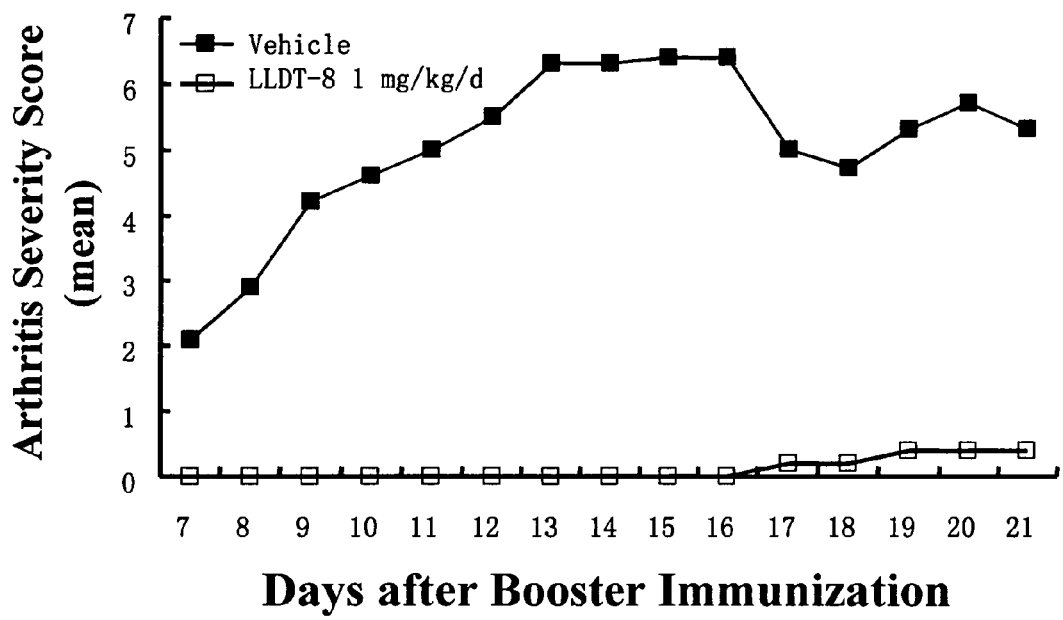
FIG. 18 shows the therapeutic effect of LLDT-8 on collagen-induced arthritis in DBA/1 mice.
Figure 19:
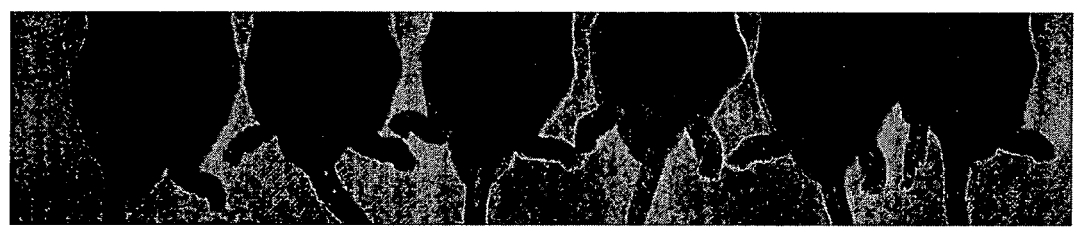
FIG. 19 shows the therapeutic effect of LLDT-8 on collagen-induced arthritis in DBA/1 mice.
Figure 19:

Results:

The murine model of bovine type II collagen-induced arthritis (CIA) in DBA/1 mice, which closely resembles the human disease, has been used extensively to increase our understanding of autoimmune-mediated arthritis and identify potential new therapeutic agents to treat rheumatoid arthritis. Administration intraperitoneally with LLDT-8 at 1 mg/Kg/d effectively reduced severity and incidence of CIA compared with untreated CIA mice (FIG. 18 and FIG. 19).

Figure 20:
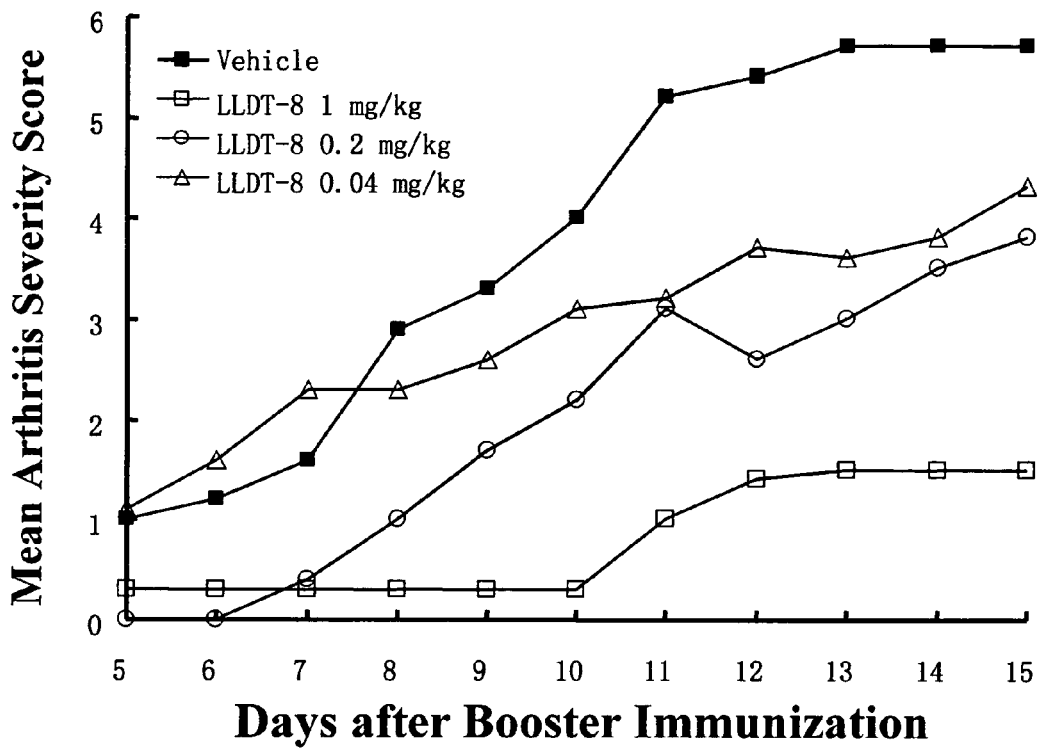
FIG. 20 shows the therapeutic effect of LLDT-8 with different dosage on collagen-induced arthritis in DBA/1 mice.

Suppressive effect was also observed in LLDT-8 treated groups with lower doses of 0.2 and 0.04 mg/Kg/d, in a dose-dependent fashion (FIG. 20).

Figure 21:
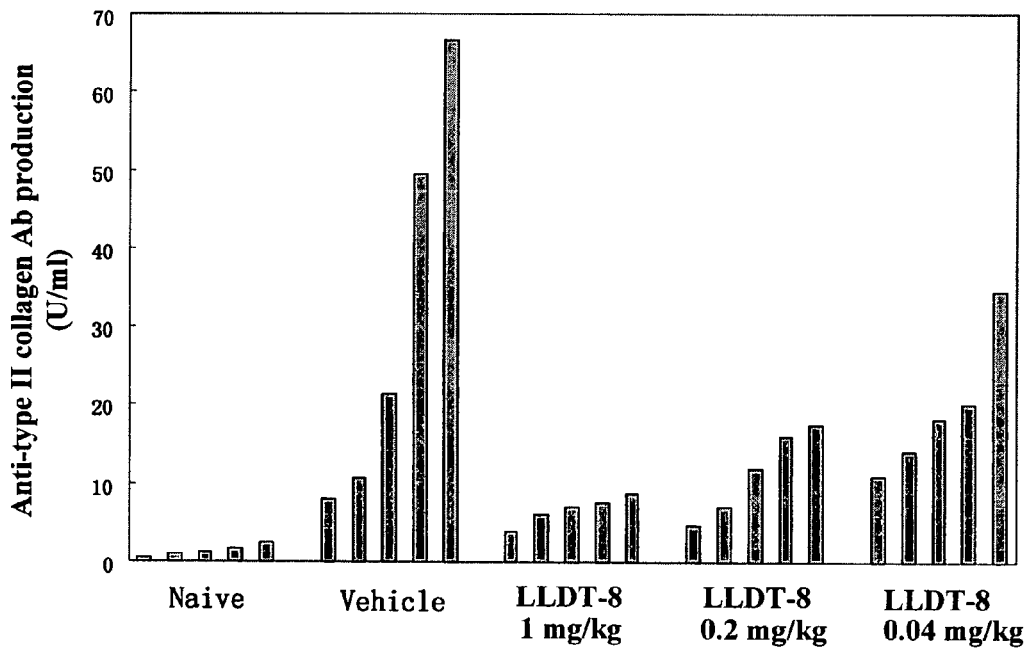
FIG. 21 shows LLDT-8 inhibited the production of anti-collagen specific antibody.

Anti-collagen specific antibody levels were reduced dose-dependently compared with untreated CIA mice. It demonstrated that LLDT-8 displayed strong inhibition in humoral immunity (FIG. 21).

Experiment 10

Effect on Murine Skin Allograft Transplantation

Method:

Full-thickness tail skin was aseptically harvested from adult C57BL/6 mice.

The skin allografts were transplanted onto the flank of adult recipient BALB/c mice.

Engrafted mice were administered LLDT-8 daily or, as a control, phosphate-buffered saline (PBS) by intraperitoneal (i.p.) injection.

Skin graft was observed daily, and time to rejection was recorded; rejection was defined as necrosis or over 50% of the graft showed sloughing or when it formed a dry scab.

Result:

The preliminary results showed that LLDT-8 prolonged murine allograft survival (C57BL/6 skin to BALB/c mice), which suggested the potential role of LLDT-8 for transplantation therapy.

Experiment 11

Anti-tumor Activity

Using regular tumor screening systems (in vitro antitumor activity), LLDT-8 was shown to have anti-tumor activity against human and murine tumor cell lines: including P-388 (murine lymphoma cell), HL-60 (human myeloblastic), A-549 (human lung carcinoma), MKN-28 (human gastric cancer), SGC-7901 (human gastric adenocarcinoma cell), MCF-7 (human breast cancer cell), BEL-7402 (human hepatic carcinoma cell), HO-8910 (human ovary cancer cells) and WI-38 (human lung fibroblasts) (Table 13).

TABLE 13

Inhibitory effect of LLDT-8 on tumor cell proliferation ($IC_{50}$/μM)

| | P-388 | HL-60 | A-549 | MKN-28 | SGC-7901 | MCF-7 | BEL-7402 | HO-8910 | WI-38 |
|---|---|---|---|---|---|---|---|---|---|
| LLDT-8 | 0.080 | 0.081 | 0.032 | 0.39 | 0.043 | 0.35 | 0.085 | 0.22 | 0.48 |

Experiment 12

Acute Toxicity (LD$_{50}$) Test in Mice

Acute Intraperitoneal Injection Toxicity

Mice were single administered with LLDT-8 by intraperitoneal injection, and observed for clinical signs of toxicity immediately and the following 14 days. Necropsy was performed on all animals that died and on all survivors at the end of the 2-week study. Death was seen from the next day after treatment and reached a peak at the 2-4 day. All gross pathological changes should be recorded for each animal. There was no gender difference in survival. No significant pathological changes were seen in tissues by gross necropsy in all survivors at day 15.

Using Bliss' method, the LD$_{50}$ of LLDT-8 was calculated to be 9.3 mg/Kg, with 95% confidence limits is 7.7-11.3 mg/Kg. LD$_{50}$ of LLDT-2 was 0.5 mg/Kg. LLDT-8 is much less toxic than its parent compound, LLDT-2.

Acute Intraperitoneal Injection Toxicity

Mice were single administered with LLDT-8 by oral, and observed for clinical signs of toxicity immediately and the following 14 days. Necropsy was performed on all animals that died and on all survivors at the end of the 2-week study. Death was seen from the next day after treatment and reached a peak at the 2-3 day. Obvious hemorrhage was seen at pylorus, duodenum, jejunum and ileum. There was no gender difference in survival. No significant pathological changes were seen in tissues by gross necropsy in all survivors at day 15.

Using Bliss' method, the LD$_{50}$ of LLDT-8 was calculated to be 6.8 mg/Kg, with 95% confidence limits is 5.4-8.4 mg/Kg.

The data hereinbefore described the structures of compounds in present invention and related bioactivity results, which can be mended without breaching the invention. The range of the mending in this invention are covered by the appendix claims.

Feasibility for the Application:

The present invention can offer new derivative from triptolide and its relative synthesis method.

The series of derivatives from triptolide, especially (5R)-5-Hydroxyltriptolide (LLDT-8), exhibits broad and potent anti-inflammatory and immunosuppressive activity, both in vitro and in vivo. It is demonstrated that LLDT8 treatment was strictly effective for prevention and therapy in many animal models of inflammatory and immune diseases. More importantly, LLDT-8 exerted immunosuppressive activity with high potency but low cytotoxicity.

During the course of the present invention it was determined that the derivatives, especially LLDT-8, or their combinations can be used as immunosuppressants for prevention and therapy against autoimmune diseases (arthritis, systemic lupus erythematosus, chronic nephritis, diabetes); inflammatory diseases (AIDS, virus hepatitis); allergy; skin diseases, cardiovascular diseases and transplant rejection, as well as anti-fertility and immune related diseases.

What is claimed is:

1. Triptolide derivatives having the structure represented by the formula (1) shown as below, or pharmaceutically acceptable salts thereof, or their optical diastereoisomers:

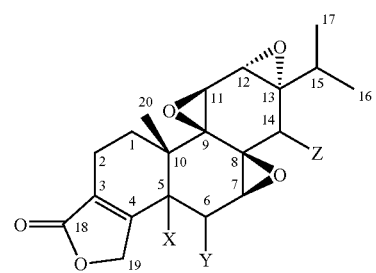

(1)

wherein X is OH (R stereochemistry), Y is OH (S stereochemistry) or H; or X and Y together form a double bond or R,S-epoxide;

Z is OH, O or OCOR, in which R is —(CH$_2$)$_n$CO$_2$Na, —(CH$_2$)$_n$CO$_2$K —(CH$_2$)nCH$_3$, n=1-6;

in the above formula (1), "—" that attaches to "X", "Y" and "Z" represents the stereochemistry orientations "◂■▪" and "▪▪▪▸" as well.

2. Triptolide derivatives according to claim 1, wherein the configuration of X is α(R), and Z is β-OH(R) shown as formula (2):

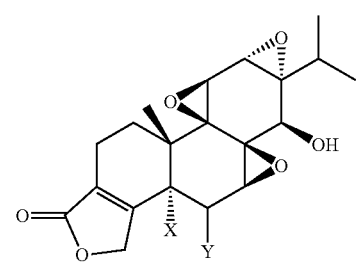

(2)

3. Triptolide derivatives according to claim 1, wherein the configuration of X is α(R), and Z is α-OH(s) shown as formula (3):

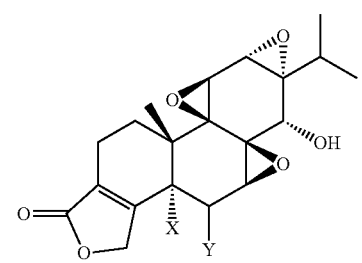

(3)

4. Triptolide derivatives according to claim 1, wherein the configuration of X is α(R), and Z is O shown as formula (4):

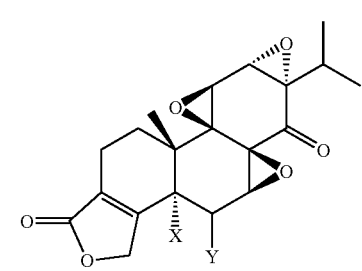

(4)

5. Triptolide derivatives according to claim 1, wherein C-5 and C-6 are connected by double bond, and the configuration of Z is R or S, or Z=O as shown formula (5):

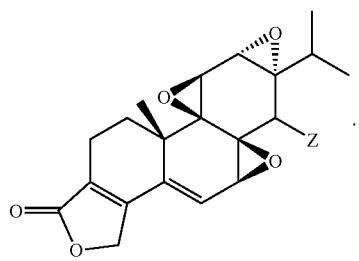

(5)

6. Triptolide derivatives according to claim 1, which comprise the following: (5R)-5-hydroxytriptonide, (5R)-5-hydroxytriptolide, (5R)-5-hydroxy-14-epitriptolide. $\Delta^{5,6}$-dehydrotriptonide, $\Delta^{5,6}$-dehydrotriptolide, $\Delta^{5,6}$-dehydro-14-epitriptolide, (5R,6S)-5,6-epoxytriptonide, (5R,6S)-5,6-epoxytriptolide, (5R,6S)-5,6-epoxy-14-epitriptolide, cis-(5R,6S)-5,6-dihydroxytriptonide, cis-(5R,6S)-5,6-dihydroxytriptolide, cis-(5R,6S)-5,6-dihydroxy-14-epitriptolide.

7. A pharmaceutical composition prepared from the triptolide derivatives of claim 1.

\* \* \* \* \*